United States Patent
Adachi et al.

(10) Patent No.: US 9,257,757 B2
(45) Date of Patent: Feb. 9, 2016

(54) CRIMP TERMINAL, CRIMP BODY, AND METHOD FOR MANUFACTURING CRIMP BODY

(71) Applicant: NGK INSULATORS, LTD., Nagoya-shi, Aichi (JP)

(72) Inventors: Yosuke Adachi, Nagoya (JP); Kenji Isaka, Nagoya (JP); Koichi Masuda, Nagoya (JP)

(73) Assignee: NGK INSULATORS, LTD., Nagoya (JP)

(*) Notice: Subject to any disclaimer, the term of this patent is extended or adjusted under 35 U.S.C. 154(b) by 0 days.

(21) Appl. No.: 14/225,544

(22) Filed: Mar. 26, 2014

(65) Prior Publication Data
US 2014/0302726 A1    Oct. 9, 2014

(30) Foreign Application Priority Data
Mar. 29, 2013 (JP) .................. 2013-073711

(51) Int. Cl.
| | |
|---|---|
| *H01R 9/24* | (2006.01) |
| *H01R 4/18* | (2006.01) |
| *G01N 27/406* | (2006.01) |
| *H01R 43/048* | (2006.01) |
| *H01R 43/16* | (2006.01) |

(52) U.S. Cl.
CPC .............. *H01R 4/18* (2013.01); *G01N 27/4062* (2013.01); *H01R 4/184* (2013.01); *H01R 43/048* (2013.01); *H01R 43/0488* (2013.01); *H01R 43/16* (2013.01); *Y10T 29/49185* (2015.01)

(58) Field of Classification Search
CPC .... H01R 43/058; H01R 13/642; H01R 4/185; H01R 13/6273; H01R 43/01; H01R 43/18; H01R 29/49185; H01R 4/184; H01R 43/0488; H01R 43/16; H01R 43/048; H01R 27/4062; Y10T 29/53226
USPC ........................................... 439/877
See application file for complete search history.

(56) References Cited

U.S. PATENT DOCUMENTS

| | | | |
|---|---|---|---|
| 4,812,138 A | 3/1989 | Kondo et al. | |
| 5,414,926 A * | 5/1995 | Ito et al. ................ | 29/753 |

(Continued)

FOREIGN PATENT DOCUMENTS

| | | |
|---|---|---|
| EP | 1739791 A1 | 1/2007 |
| JP | 5-190214 A | 7/1993 |

(Continued)

OTHER PUBLICATIONS

Extended European Search Report for the corresponding European patent application No. 14161881.9 issued on Jul. 16, 2014.

*Primary Examiner* — Jean F Duverne
(74) *Attorney, Agent, or Firm* — Global IP Counselors, LLP

(57) ABSTRACT

In a holding portion of a contact fitting, in a state before crimping of core wires, the thickness of a first distal end portion and the thickness of a second distal end portion are both 70% or less of the thickness of the bottom portion. The thicknesses are both smaller than the diameter of core wires of a lead wire to be crimped. The first distal end portion and the second distal end portion are formed by compression processing. Using the holding portion, a first side portion and a second side portion are curved such that they face the bottom portion, and the plurality of core wires are surrounded and crimped with the bottom portion, the first side portion, and the second side portion.

12 Claims, 12 Drawing Sheets

(56) References Cited

U.S. PATENT DOCUMENTS

| | | | |
|---|---|---|---|
| 5,484,961 A * | 1/1996 | Itoh et al. | 174/84 C |
| 5,486,653 A * | 1/1996 | Dohi | 174/84 C |
| 5,500,999 A * | 3/1996 | Yagi et al. | 29/753 |
| 8,826,523 B2 * | 9/2014 | Takahashi et al. | 29/753 |
| 8,984,925 B2 * | 3/2015 | Battenfeld | 72/412 |
| 2006/0288757 A1 | 12/2006 | Nishio et al. | |
| 2008/0172874 A1 | 7/2008 | Yagi et al. | |
| 2008/0176458 A1 | 7/2008 | Yagi et al. | |
| 2011/0034091 A1 | 2/2011 | Kobayashi et al. | |

FOREIGN PATENT DOCUMENTS

| | | |
|---|---|---|
| JP | 2007-5202 A | 1/2007 |
| JP | 2008-177028 A | 7/2008 |
| JP | 2008-181713 A | 8/2008 |
| JP | 2011-40194 A | 2/2011 |

* cited by examiner

CRIMP TERMINAL, CRIMP BODY, AND METHOD FOR MANUFACTURING CRIMP BODY

CROSS-REFERENCE TO RELATED APPLICATIONS

This application claims priority to Japanese Patent Application No. 2013-073711 filed on Mar. 29, 2013, the entirety of which is hereby incorporated by reference in its entirety.

BACKGROUND

1. Field of the Invention

The present invention relates to a crimp terminal, a crimp body, and a method for manufacturing a crimp body.

2. Description of Related Art

Hitherto, there has been known a crimp terminal having a fixing portion that fixes core wires of a lead wire. For example, Japanese Unexamined Patent Application Publication No. 2007-5202 describes a crimp terminal including a fixing portion having a bottom wall and a pair of side walls erected from both ends of the bottom wall, wherein both distal end parts of the side walls that are located on the side opposite to the bottom wall are bent toward the bottom wall, and wherein an enclosing portion surrounding core wires of a lead wire is formed by the bottom wall and both the side walls. Japanese Unexamined Patent Application Publication No. 2007-5202 describes that when the relationship between the maximum width of the fixing portion, the maximum width of the enclosing portion, and the minimum thickness of the bottom wall and the relationship between the maximum height from the bottom wall to the starting point of the side wall farthest from the bottom wall and the maximum height from the starting point to the end of each distal end part satisfy predetermined conditions, the core wires of the lead wire can be fixed firmly.

SUMMARY

When a crimp terminal cannot fix core wires of a lead wire firmly, for example, the lead wire may be prone to come off after crimping. In addition, insufficiency of the adhesion between the crimp terminal and the core wires and the adhesion between the core wires may cause variation in the contact resistance in the crimp terminal part. So, it has been desired to fix core wires of a lead wire more firmly.

The present invention has been made to solve such a problem, and it is a main object of the present invention to fix core wires of a lead wire more firmly.

A crimp terminal in the present invention comprises a holding portion including a bottom portion, a first side portion continuous with the bottom portion, and a second side portion continuous with the side of the bottom portion opposite to the first side portion, wherein the first side portion has a first distal end portion located at the end on the side opposite to the side continuous with the bottom portion, and the thickness of the first distal end portion is 70% or less of the thickness of the bottom portion, and wherein the second side portion has a second distal end portion located at the end on the side opposite to the side continuous with the bottom portion, and the thickness of the second distal end portion is 70% or less of the thickness of the bottom portion.

In the crimp terminal of the present invention, the thickness of the first distal end portion of the first side portion is 70% or less of the thickness of the bottom portion, and the thickness of the second distal end portion of the second side portion is 70% or less of the thickness of the bottom portion. The holding portion of the crimp terminal can surround and crimp a plurality of core wires of a lead wire with the bottom portion, the first side portion, and the second side portion by curving the first side portion and the second side portion such that the first distal end portion and the second distal end portion face the bottom portion. When performing crimping in this manner, the first distal end portion and the second distal end portion easily bite into the plurality of core wires since the thicknesses of the first distal end portion and the second distal end portion are 70% or less of the thickness of the bottom portion. Therefore, the core wires of the lead wire can be fixed more firmly with the bottom portion, the first side portion, and the second side portion. The smaller the thickness of the first distal end portion and the thickness of the second distal end portion, the more easily the first and second distal end portions bite into the plurality of core wires. However, from the manufacturing viewpoint and the viewpoint of the strength of the first and second distal end portions, the thickness of the first distal end portion and the thickness of the second distal end portion are preferably 40% or more of the thickness of the bottom portion. In the state after the core wires are crimped by the crimp terminal, the thickness of the first distal end portion does not necessarily have to be 70% or less of the thickness of the bottom portion, and the thickness of the second distal end portion does not necessarily have to be 70% or less of the thickness of the bottom portion. In the crimp terminal of the present invention, the thicknesses of the first distal end portion and the second distal end portion may be smaller than the diameter of the core wires of the lead wire to be crimped. In this case, at the time of crimping, the first distal end portion and the second distal end portion bite into the plurality of core wires more easily. In the state after the core wires are crimped by the crimp terminal, the thicknesses of the first distal end portion and the second distal end portion do not necessarily have to be smaller than the diameter of the core wires of the lead wire that are crimped.

In the crimp terminal of the present invention, the first distal end portion and the second distal end portion may be formed by compression processing. In this case, the strength of the first and second distal end portions can be made high compared to the case where the first and second distal end portions are thinned, for example, by polishing or grinding. When the first and the second distal end portions are thinned by processing not limited to compression processing, the thicknesses of the first and the second distal end portions after processing may be 70% or less of the thicknesses before processing.

A crimp body in the present invention comprises a lead wire having a plurality of core wires; and a crimp terminal comprising a holding portion including a bottom portion, a curved first side portion continuous with the bottom portion, and a curved second side portion continuous with the side of the bottom portion opposite to the first side portion, the first side portion and the second side portion are curved such that a first distal end portion that is the distal end portion of the first side portion and a second distal end portion that is the distal end portion of the second side portion face the bottom portion, and the holding portion thereby surrounds and crimps the plurality of core wires with the bottom portion, the first side portion, and the second side portion, and when the holding portion is viewed in a section perpendicular to the axial direction of the core wires, in the section, horizontal direction is defined as the direction of a tangent to the curved part of the first side portion and the curved part of the second side portion, height direction is defined as the direction perpendicular to the horizontal direction, a crimp height CH that is the height from the bottom surface of the bottom portion to the tangent is 1.20±0.05 mm and a crimp width CW that is the width in the horizontal direction of the holding portion is 1.66±0.05 mm.

In the crimp body of the present invention, the holding portion is sufficiently compressed in the height direction since the crimp height CH is 1.20±0.05 mm and the crimp width CW is 1.66±0.05 mm in the section of the holding portion. Therefore, the core wires of the lead wire can be fixed more firmly. In this case, the first distal end portion and the second distal end portion may bite into the plurality of core wires. Here, "the first side portion and the second side portion are curved such that a first distal end portion that is the distal end portion of the first side portion and a second distal end portion that is the distal end portion of the second side portion face the bottom portion" describes the direction of the curvature of the first side portion 72 and the second side portion 73. Therefore, the crimp bodies of the present invention also include a crimp body in which the first distal end portion and the second distal end portion do not face the bottom portion 74 in a state after crimping.

In the crimp body of the present invention, in the section, a height Ha that is the distance in the height direction of the contact part between the first side portion and the second side portion may be 0.15 mm or more. In this case, the contact (crimping) between the first side portion and the second side portion is sufficient, and the core wires of the lead wire can be fixed more firmly.

In the crimp body of the present invention, in the section, an angle α that is the angle between the contact part between the first side portion and the second side portion and the height direction may be 0° or more and 30° or less. In this case, the first side portion and the second side portion can crimp the core wires in a balanced manner, and the core wires of the lead wire can be fixed more firmly.

In the crimp body of the present invention, in the section, a distance CFA that is the minimum distance in the height direction between the lowermost part of a surface of the bottom portion on the side of the core wires, and the first distal end portion side of the first side portion and the second distal end portion side of the second side portion may be 0.125 mm or more. When the distance CFA is less than 0.125 mm, the distance between at least one of the first distal end portion side of the first side portion and the second distal end portion side of the second side portion and the bottom portion is small, and some of the core wires may be excessively crushed. This can be prevented by making the distance CFA 0.125 mm or more. That is, by making the distance CFA 0.125 mm or more, the plurality of core wires can be crimped in a balanced manner, and the core wires of the lead wire can be fixed more firmly.

In the crimp body of the present invention, in the section, a distance CFE that is the distance in the height direction between the tangent in the horizontal direction to the first distal end portion side of the first side portion and the tangent in the horizontal direction to the second distal end portion side of the second side portion may be 0 mm or more and 0.25 mm or less. In this case, the first side portion and the second side portion can crimp the core wires in a balanced manner, and the core wires of the lead wire can be fixed more firmly. The smaller the value of the distance CFE, the more preferable.

In the crimp body of the present invention, in the section, when compression rate CR [%]=(the area of the region surrounded by the bottom portion, the first side portion, and the second side portion)/{(the cross-sectional area of each core wire before crimping)×(the number of the crimped core wires)}×100, the compression rate CR [%] may be 87% or less. In this case, the crimp terminal compresses the core wires sufficiently, and the core wires of the lead wire can be fixed more firmly. The lower the compression rate CR, the more firmly the core wires can be fixed. The lower limit of the compression rate CR is determined by, for example, the material and number of the core wires and the force applied during crimping. The compression rate CR may be, for example, 50% or more.

In the crimp body of the present invention, in the section, it is preferable that no cracks are generated in rising parts on the side of the core wires from the bottom portion to the first side portion and the second side portion. In this case, compared to the case where cracks are generated, the strength of the holding portion is high, and therefore the core wires of the lead wire can be fixed more firmly.

In the crimp body of the present invention, in the section, a burr height Gh that is the height of a burr on the bottom portion may be 0 mm or more and 0.25 mm or less, and the burr may be within a region that is closer to the core wires than the lowermost part of the bottom portion in the height direction. When crimping the core wires using the crimp terminal, a burr may be generated on the bottom portion. This burr contributes little to the fixing of the core wires. The larger the burr, the higher the percentage of part of the member forming the bottom portion and the first and second side portions that does not affect the fixing of the core wires, and therefore the more insufficient the fixing of the core wires. The larger the burr, the more likely the burr is to damage members around the holding portion (for example, a sheath of another lead wire, and a rubber plug that seals the area around the holding portion). When the burr height Gh is 0 mm or more and 0.25 mm or less, such an effect of the burr can be made relatively small. The smaller the value of the burr height Gh, the more preferable. The fact that the burr height Gh is 0 mm means that no burr is generated. When there are a plurality of burrs, it is preferable that the burr heights Gh of the plurality of burrs be all 0 mm or more and 0.25 mm or less.

In the crimp body of the present invention, in the section, a burr width Gb that is the width in the horizontal direction of a burr on the bottom portion may be 0 mm or more and 0.125 mm or less. When the burr width Gb is 0 mm or more and 0.125 mm or less, the above-described effect of the burr can be made relatively small. The smaller the value of the burr width Gb, the more preferable. The fact that the burr width Gb is 0 mm means that no burr is generated. When there are a plurality of burrs, it is preferable that the burr widths Gb of the plurality of burrs be all 0 mm or more and 0.125 mm or less.

In the crimp body of the present invention, in the section, a bottom portion thickness Sb that is the thickness of the bottom portion may be 0.1875 mm or more. In this case, the strength of the bottom portion is higher, and therefore the core wires of the lead wire can be fixed more firmly.

The crimp body of the present invention described above can be obtained relatively easily, for example, by crimping a plurality of core wires using the crimp terminal of the present invention described above.

A method for manufacturing a crimp body includes a crimp terminal including a holding portion including a bottom portion, a first side portion continuous with the bottom portion, and a second side portion continuous with the side of the bottom portion opposite to the first side portion, wherein the first side portion has a first distal end portion located at the end on the side opposite to the side continuous with the bottom portion, and the thickness of the first distal end portion is 70% or less of the thickness of the bottom portion, and wherein the second side portion has a second distal end portion located at the end on the side opposite to the side continuous with the bottom portion, and the thickness of the second distal end portion is 70% or less of the thickness of the bottom portion, the method comprising the steps of:

(a) preparing the crimp terminal and a lead wire having a plurality of core wires; and (b) surrounding and crimping the plurality of core wires with the bottom portion, the first side portion, and the second side portion by curving the first side portion and the second side portion such that the first distal end portion and the second distal end portion face the bottom portion.

In the method for manufacturing a crimp body of the present invention, a crimp terminal in which, as with the crimp terminal of the present invention described above, the thickness of the first distal end portion is 70% or less of the thickness of the bottom portion and the thickness of the second distal end portion is 70% or less of the thickness of the bottom portion is prepared, and crimping of the plurality of core wires is performed using this. That is, in a state before crimping, the thickness of the first distal end portion of the first side portion is 70% or less of the thickness of the bottom portion, and the thickness of the second distal end portion of the second side portion is 70% or less of the thickness of the bottom portion. Using this crimp terminal, the first side portion and the second side portion are curved such that the first distal end portion and the second distal end portion face the bottom portion, and the plurality of core wires are surrounded and crimped with the bottom portion, the first side portion, and the second side portion. Therefore, the first distal end portion and the second distal end portion easily bite into the plurality of core wires, and the core wires of the lead wire can be fixed more firmly with the bottom portion, the first side portion, and the second side portion.

In the method for manufacturing a crimp body of the present invention, in the step (a), the crimp terminal in which the thicknesses of the first distal end portion and the second distal end portion are smaller than the diameter of the core wires of the lead wire may be prepared. In this case, in the step of crimping, the first distal end portion and the second distal end portion bite into the plurality of core wires more easily.

BRIEF DESCRIPTION OF THE DRAWINGS

Referring now to the attached drawings which form a part of this original disclosure.

DETAILED DESCRIPTION OF EMBODIMENTS

Embodiments for carrying out the present invention will now be described with reference to the drawings.

Figure 1:
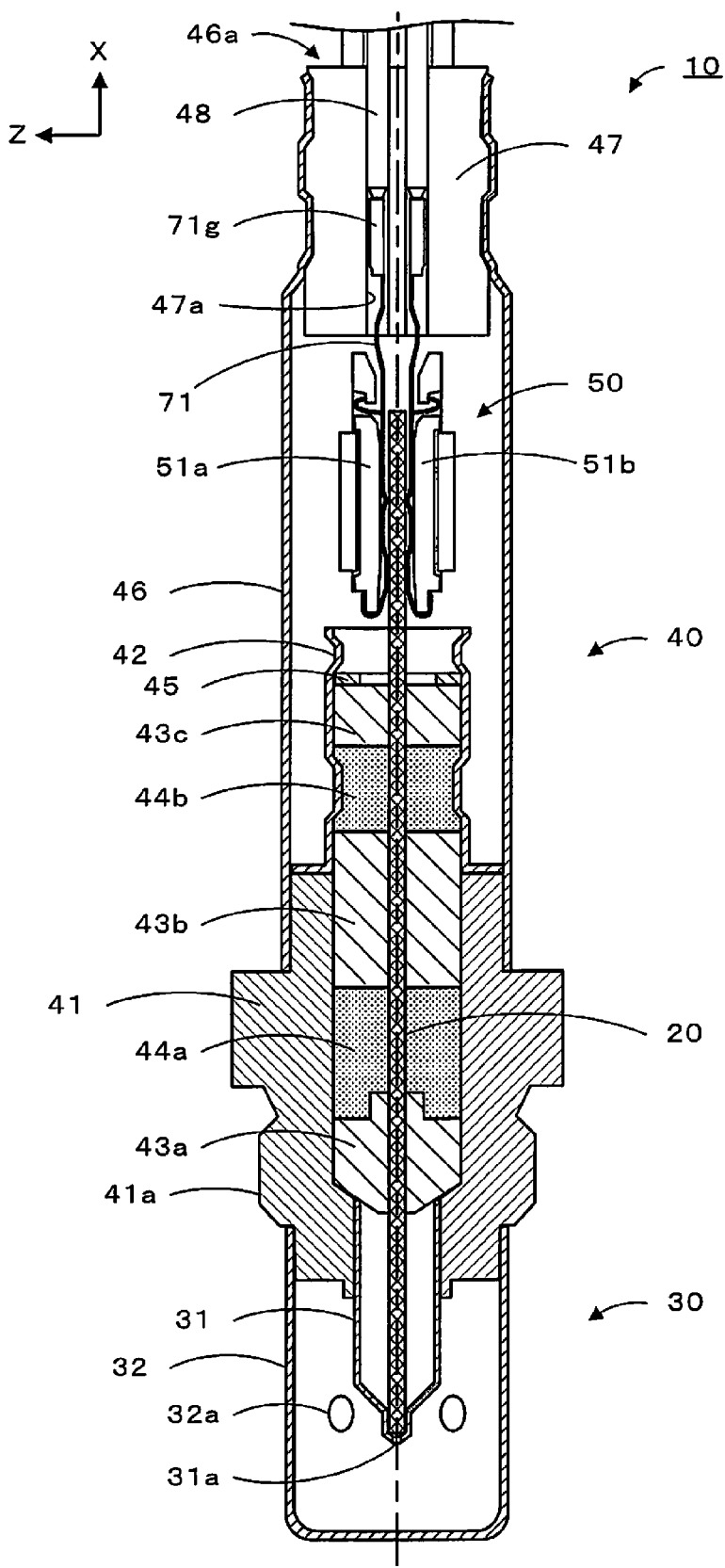
FIG. 1 is a longitudinal sectional view of a gas sensor 10 of the embodiment.
Figure 2:
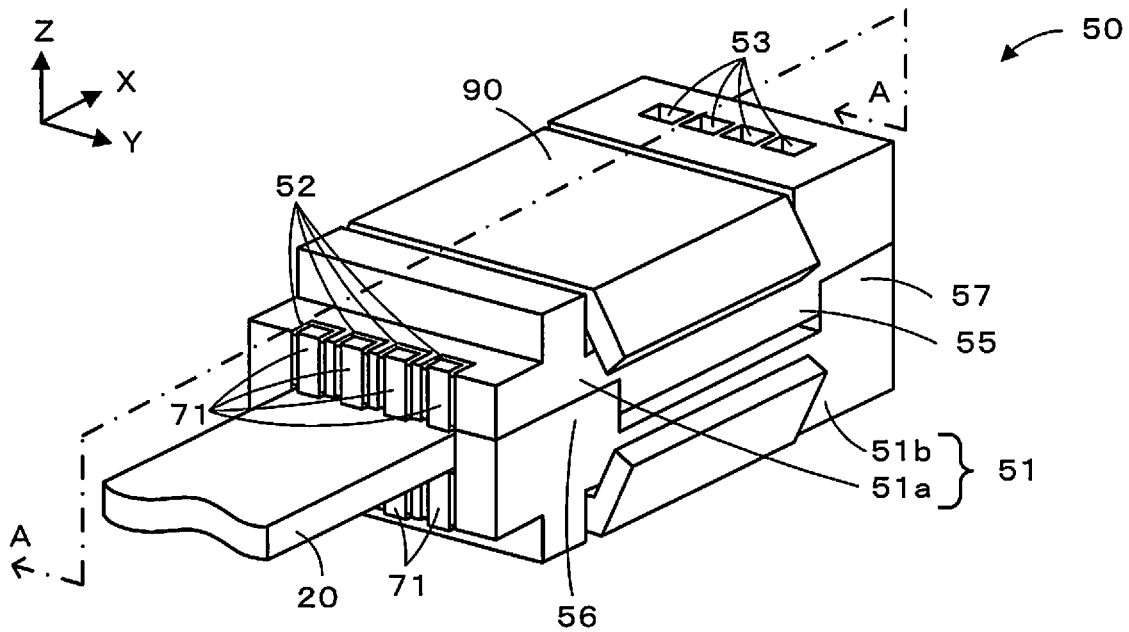
FIG. 2 is a perspective view of a connector 50.
Figure 3:
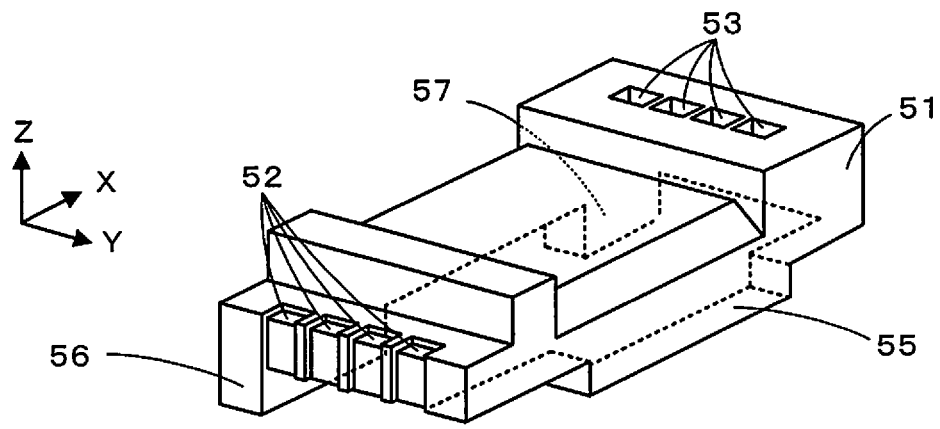
FIG. 3 is an exploded perspective view showing a housing 51 of the connector 50.
Figure 4:
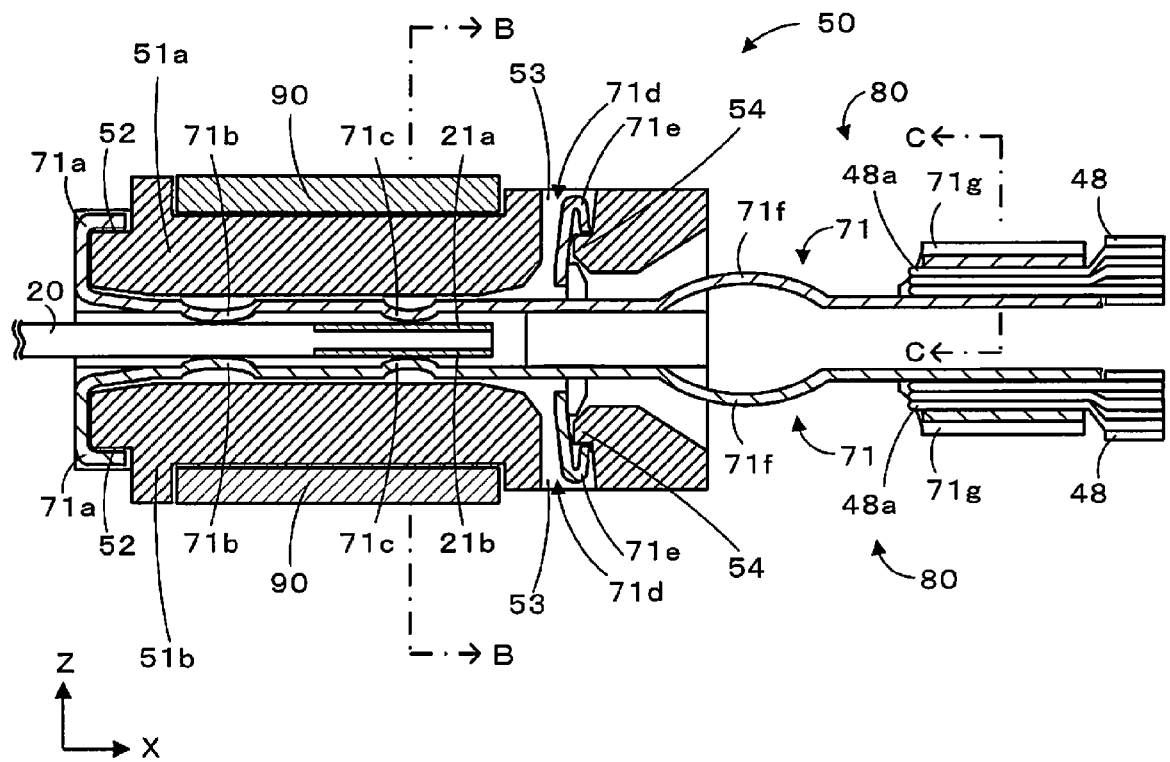
FIG. 4 is a sectional view taken along line A-A of FIG. 2.
Figure 5:
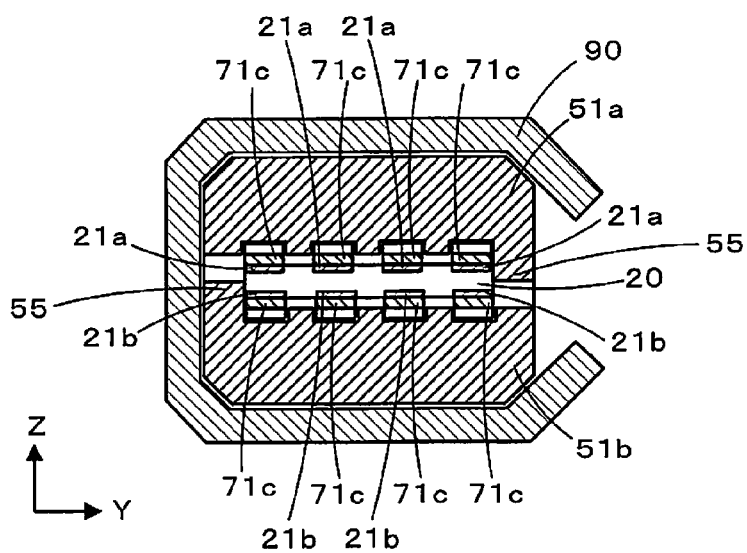
FIG. 5 is a sectional view taken along line B-B of FIG. 4.
Figure 6:
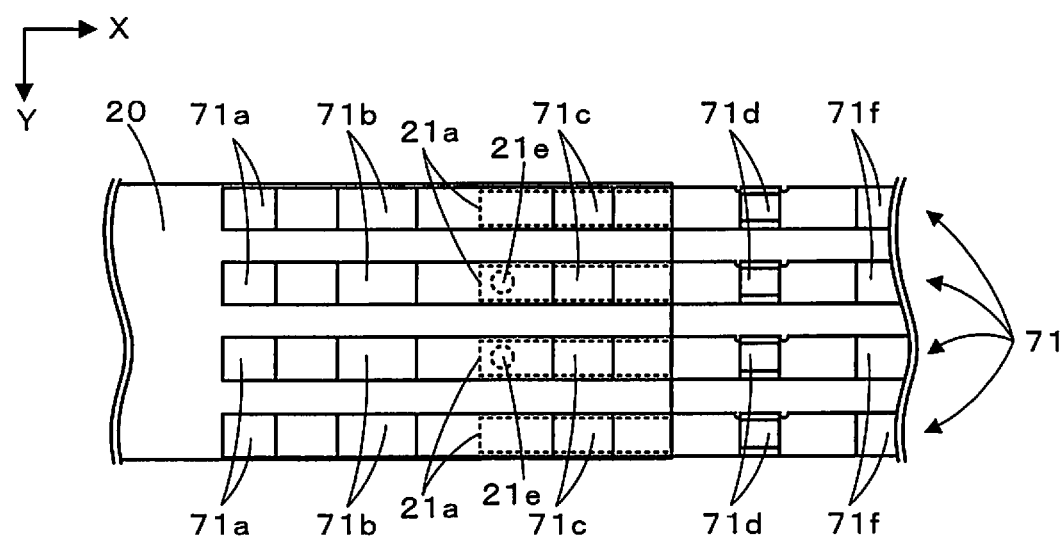
FIG. 6 is an explanatory diagram showing the positional relationship between contact fittings 71 and a sensor element 20 as viewed from the first housing 51a side.

FIG. 1 is a longitudinal sectional view of a gas sensor 10 having a contact fitting 71 that is an embodiment of a crimp terminal of the present invention. FIG. 2 is a perspective view of a connector 50, and FIG. 3 is an exploded perspective view showing a housing 51 of the connector 50. FIG. 4 is a sectional view taken along line A-A of FIG. 2, FIG. 5 is a sectional view taken along line B-B of FIG. 4, and FIG. 6 is an explanatory diagram showing the positional relationship between contact fittings 71 and a sensor element 20 as viewed from a first housing 51a side.

As shown in FIG. 1, the gas sensor 10 includes the sensor element 20 that measures a predetermined gas component in gas to be measured, a protective cover 30 that protects one end of the sensor element 20, and a sensor assembly 40 that includes the connector 50 electrically connected to the sensor element 20. The gas sensor 10 is attached, for example, to an exhaust gas pipe of a vehicle, and is used to measure gas components such as NOx and $O_2$ contained in exhaust gas as gas to be measured.

The sensor element 20 is an elongated element having a plate-like shape, and is formed by laminating, for example, six ceramic substrates that are oxygen ion conductive solid electrolyte layers of zirconia ($ZrO_2$) or the like. The end of the sensor element 20 that is closest to the protective cover 30 will be referred to as distal end, and the end of the sensor element 20 that is closest to the connector 50 will be referred to as proximal end. On surfaces (a first surface that is the upper surface in FIG. 5 and a second surface that is the lower surface in FIG. 5) of the proximal end of the sensor element 20, four first surface electrodes 21a and four second surface electrodes 21b are formed as shown in FIG. 5. The first surface electrodes 21a and the second surface electrodes 21b will be collectively referred to as electrodes 21. The electrodes 21 are for applying a voltage to the sensor element 20, and for taking out electromotive force or current generated according to the concentration of a gas component detected by the sensor element 20, and are electrically connected through electrical paths inside the sensor element 20 to electrodes (not shown) in the distal end of the sensor element 20. The positions of the first surface electrodes 21a and the second surface electrodes 21b will be described later.

The protective cover 30 is disposed so as to surround the distal end of the sensor element 20 as shown in FIG. 1. The protective cover 30 includes an inner protective cover 31 that covers the distal end of the sensor element 20, and an outer protective cover 32 that covers the inner protective cover 31. The inner protective cover 31 is formed in a cylindrical shape, and has an inner protective cover hole 31a for introducing gas to be measured to the distal end of the sensor element 20. The outer protective cover 32 is formed in a bottomed cylindrical shape, and has, in the side surface thereof, outer protective cover holes 32a for introducing gas to be measured. The inner protective cover 31 and the outer protective cover 32 are made of metal such as stainless steel.

The sensor assembly 40 includes a main fitting 41 made of meal, an inner cylinder 42 and an outer cylinder 46 that are cylindrical and that are fixed to the main fitting 41 by welding, and the connector 50 connected to the proximal end of the sensor element 20. The main fitting 41 can be attached, for example, to an exhaust gas pipe of a vehicle with an external thread portion 41a. A plurality of ceramic supporters 43a to 43c, and ceramic powder 44a and 44b such as talc filling the space between the ceramic supporters 43a and 43b and the space between the ceramic supporters 43b and 43c are enclosed within the inner cylinder 42, and these are sealed between a metal ring 45 and the inner wall of the main fitting 41. The outer cylinder 46 covers the peripheries of the inner cylinder 42, the sensor element 20, and the connector 50, and lead wires 48 connected to the connector 50 are pulled out through an open end 46a to the outside. The lead wires 48 are electrically connected through the connector 50 to the electrodes 21 of the sensor element 20. Gaps between the outer cylinder 46 and the lead wires 48 are sealed by a rubber plug 47.

Next, the connector 50 will be described in detail. As shown, the connector 50 includes the first housing 51a and a second housing 51b that are made of ceramic such as sintered alumina body, the contact fittings 71 that are held by the first housing 51a or the second housing 51b and that face and are in contact with the electrodes 21 of the sensor element 20 on a one-to-one basis, and a metal clamp 90 that clamps and fixes the first housing 51a and the second housing 51b.

The first housing 51a and the second housing 51b are members that each hold four contact fittings 71 arranged in a direction (Y direction) perpendicular to the longitudinal direction of the contact fittings 71 (X direction). The first housing 51a and the second housing 51b have the same shape, so the same reference numerals will be used to designate the same components in the first housing 51a and the second housing 51b. The first housing 51a and the second housing 51b will be collectively referred to as housings 51. Each housing 51 includes four locking grooves 52 that lock the contact fittings 71, four insertion holes 53 into which the contact fittings 71 are inserted, and locking portions 54 (see FIG. 4) formed in the insertion holes 53 and locking the contact fittings 71. Each housing 51 has a protruding portion 55 on one side thereof in the Y direction, and restricting members 56 and 57 that restrict the distance in the Z direction between the first housing 51a and the second housing 51b on the other side thereof, with the sensor element 20 interposed therebetween (see FIG. 2 and FIG. 3). The protruding portion 55 is inserted into the recess between the restricting member 56 and the restricting member 57 of the opposite housing 51, and the relative positions of the first housing 51a and the second housing 51b in the X direction can thereby be fixed.

The contact fittings 71 are metal members held by the housings 51 at positions facing the electrodes 21 of the sensor element 20 on a one-to-one basis, and each include, as shown in FIG. 4, a distal end portion 71a that has a curved shape and that is thereby locked in the locking groove 52, a supporting portion 71b that is curved and protruded toward the sensor element 20, a conduction portion 71c that is curved and protruded toward the sensor element 20 and that is thereby in contact with the electrode 21, an upright portion 71d that is inserted into the insertion hole 53, a curved portion 71f that is pulled out to the outside of the connector 50, and a holding portion 71g that crimps and holds a plurality of core wires 48a of a lead wire 48 outside the connector 50. The holding portion 71g and the lead wire 48 crimped by the holding portion 71g will be collectively referred to as crimp body 80. The supporting portion 71b and the conduction portion 71c are arranged along the longitudinal direction of the contact fitting 71 (the X direction in FIG. 4), and the conduction portion 71c is disposed at a position closer to the holding portion 71g than the supporting portion 71b. The supporting portion 71b and the conduction portion 71c are both formed so as to be able to be elastically deformed, and both have a spring constant within a range, for example, of 500 to 4000 N/mm. The upright portion 71d has a hook portion 71e that has a curved shape and that is thereby locked to the locking portion 54. The conduction portions 71c of the contact fittings 71 held by the first housing 51a face and are in contact with the first surface electrodes 21a of the sensor element 20 on a one-to-one basis, and the conduction portions 71c of the contact fittings 71 held by the second housing 51b face and are in contact with the second surface electrodes 21b of the sensor element 20 on a one-to-one basis (see FIG. 4 and FIG. 5).

The positional relationship between the contact fittings 71 and the electrodes 21 of the sensor element 20 will be described. As shown in FIG. 4 and FIG. 6, the first surface electrodes 21a of the sensor element 20 extend from the proximal end of the sensor element 20 (the right end in FIG. 4 and FIG. 6) to a position between the conduction portions 71c and the supporting portions 71b. Of the four first surface electrodes 21a arranged in the Y direction, the central two first surface electrodes 21a are electrically connected to through holes 21e that are formed for electrical connection to the above-described electrical paths inside the sensor element 20. As shown in FIG. 6, each through hole 21e is formed at a position between the conduction portion 71c and the supporting portion 71b. The positional relationship between the second surface electrodes 21b and the contact fittings 71, and the positions of through holes 21e electrically connected to the second surface electrodes 21b are the same as this, so the description thereof will be omitted.

Figure 7A:
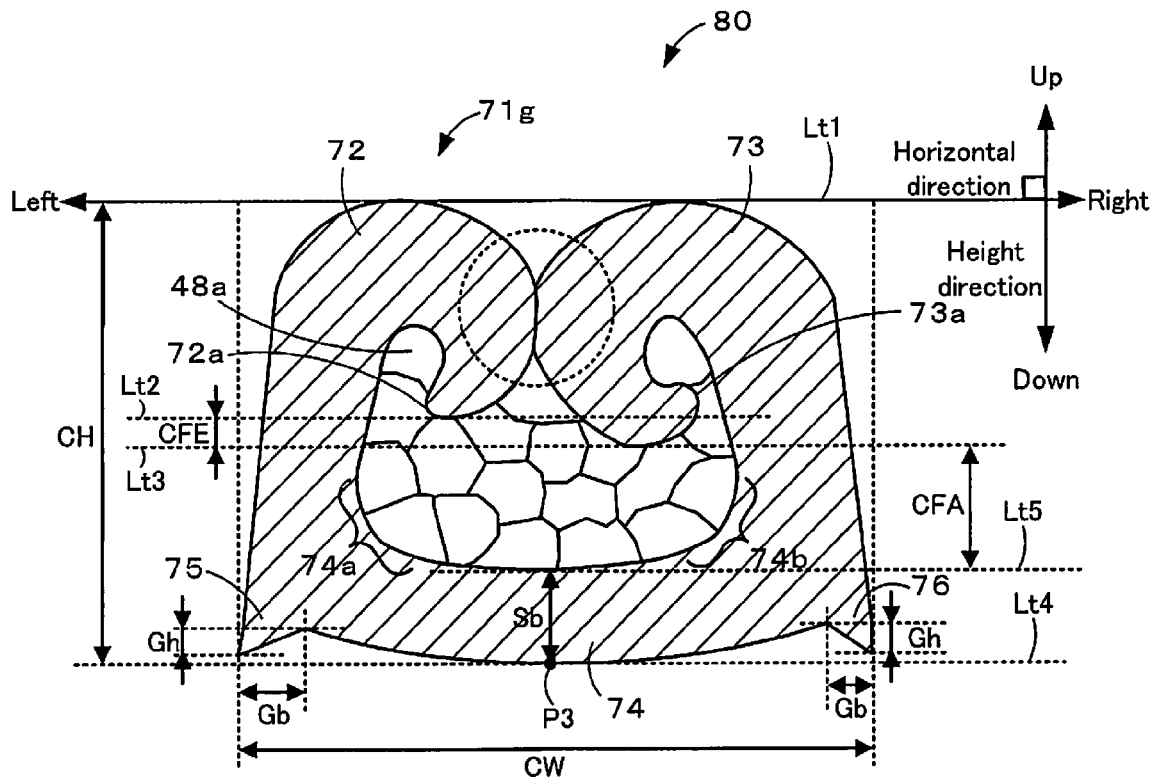
FIG. 7 is a sectional view taken along line C-C of FIG. 4.
Figure 7B:
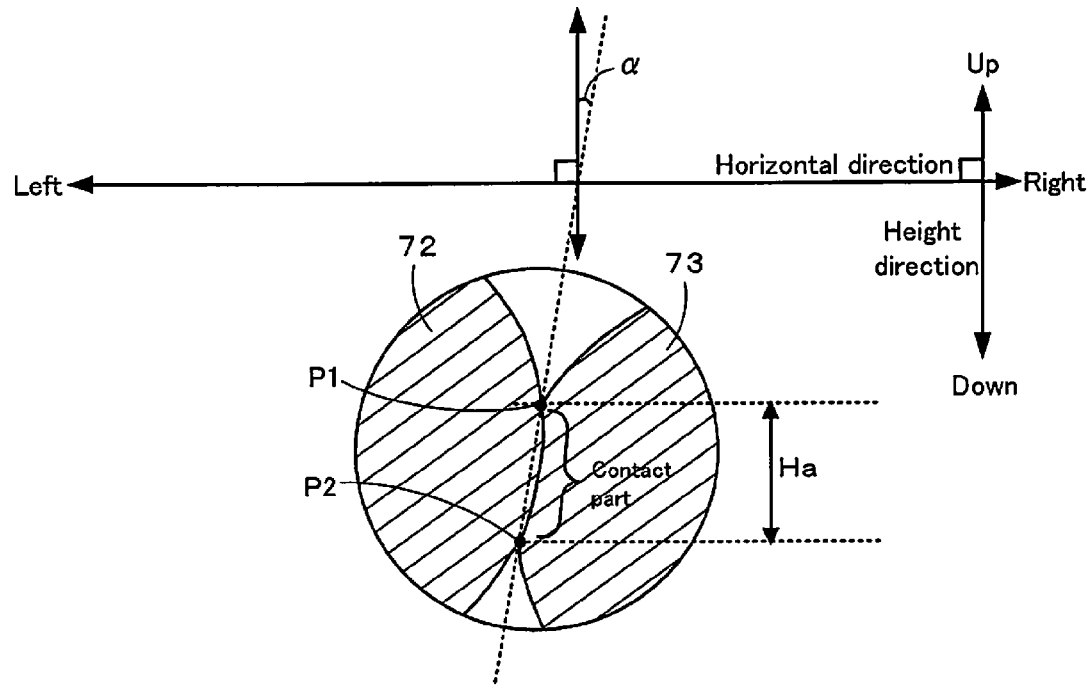

The holding portion 71g of the contact fitting 71 will be described in detail. FIG. 7 is a sectional view taken along line C-C of FIG. 4. FIG. 7 is a section perpendicular to the axial direction of the core wires 48a (the X direction in FIG. 4). FIG. 7A is an explanatory diagram showing the whole section of the holding portion 71g, and FIG. 7B is an enlarged view of the contact part between the first side portion 72 and the second side portion 73 in FIG. 7A (the part surrounded by the dashed circle). As shown in FIG. 7A, the holding portion 71g includes a bottom portion 74, a first side portion 72 that is continuous with the bottom portion 74 and that is erected from the bottom portion 74, and a second side portion 73 that is continuous with the bottom portion 74 and that is erected from the bottom portion 74. The first side portion 72 is continuous with the left side of the bottom portion 74 in FIG. 7, and the second side portion 73 is continuous with the side of the bottom portion 74 opposite to the first side portion 72 (the right side in FIG. 7). The first side portion 72 has a first distal end portion 72a located at the end on the side opposite to the side continuous with the bottom portion 74. The second side portion 73 has a second distal end portion 73a located at the end on the side opposite to the side continuous with the bottom portion 74.

In the holding portion 71g, in the section shown in FIG. 7, the first side portion 72 and the second side portion 73 are curved such that the first distal end portion 72a of the first side portion 72 and the second distal end portion 73a of the second side portion 73 face the bottom portion 74. A plurality of (19 in this embodiment) core wires are thereby surrounded and crimped with the bottom portion 74, the first side portion 72, and the second side portion 73. By this crimping, the holding portion 71g and the core wires 48 are electrically connected with each other, and form a crimp body 80 including the holding portion 71g and the lead wire 48. The part of the first side portion 72 on the side opposite to the bottom portion 74 and the part of the second side portion 73 on the side opposite to the bottom portion 74 are curved so as to approach each other. The first distal end portion 72a and the second distal end portion 73a bite into the plurality of core wires 48a of the lead wire 48. "The first side portion 72 and the second side portion 73 are curved such that the first distal end portion 72a of the first side portion 72 and the second distal end portion 73a of the second side portion 73 'face the bottom portion 74'" describes the direction of curvature of the first side portion 72 and the second side portion 73, and the first distal end portion 72a and the second distal end portion 73a do not necessarily have to face the bottom portion 74 in the state after crimping. For example, like the second distal end portion 73a in FIG. 7A, they may face in a direction different from the direction toward the bottom portion 74 (to the upper right in the figure).

The holding portion 71g is formed so as to satisfy predetermined first to tenth conditions in the section shown in FIG. 7. The first to tenth conditions will be described with reference to FIG. 7 below. First, as a premise, the horizontal direction and height direction in the section shown in FIG. 7 will be defined. First, horizontal direction is defined as the direction of a tangent Lt1 to the curved part of the first side portion 72 and the curved part of the second side portion 73 in the section shown in FIG. 7. The tangent Lt1 to the curved part of the first side portion 72 and the curved part of the second side portion 73 is a line connecting the vertices of the curved parts of the first side portion 72 and the second side portion 73 on the side far from the bottom portion 74 (the upper side in FIG. 7) as shown in FIG. 7A. In the horizontal direction, the side of the first side portion 72 will be referred to as leftward direction, and the side of the second side portion 73 will be referred to as rightward direction. Height direction is defined as the direction perpendicular to the horizontal direction. In the height direction, the side of the bottom portion 74 will be referred to as downward direction, and the side of the first side portion 72 and the second side portion 73 will be referred to as upward direction.

The first condition is that "the crimp height CH is 1.20±0.05 mm, and the crimp width is 1.66±0.05 mm." Here, the crimp height CH is the height from the bottom surface of the bottom portion 74 to the tangent Lt (see FIG. 7A). The crimp width CW is the width in the horizontal direction of the holding portion 71g (see FIG. 7A).

The second condition is that "the height Ha is 0.15 mm or more." Here, the height Ha is the distance in the height direction of the contact part between the first side portion 72 and the second side portion 73 (see FIG. 7B). In FIG. 7B, points P1 and P2 are the ends of the contact part between the first side portion 72 and the second side portion 73. Therefore, the height Ha can be obtained as the distance in the height direction between the points P1 and P2. The height Ha, although it is not particularly limited, may be, for example, 0.30 mm or less.

The third condition is that "the angle α is 0° or more and 30° or less." Here, the angle α is the angle between the contact part between the first side portion 72 and the second side portion 73 and the height direction (see FIG. 7B). As shown in FIG. 7B, the contact part between the first side portion 72 and the second side portion 73 is not limited to a straight line and can be a curved line. So, the angle α is defined as the angle between the straight line connecting the points P1 and P2 at both ends of the contact part and the height direction.

The fourth condition is that "the distance CFA is 0.125 mm or more." Here, the distance CFA is the minimum distance in the height direction between the lowermost part (the lowermost part in FIG. 7A) of the surface of the bottom portion 74 on the side of the core wires (the upper surface of the bottom portion 74 in FIG. 7A), and the first distal end portion 72a side of the first side portion 72 and the second distal end portion 73a side of the second side portion 73 (see FIG. 7A). In other words, the distance CFA is the distance between the tangent Lt5 parallel to the horizontal direction to the lowermost part of the upper surface of the bottom portion 74, and one of the tangent Lt 2 in the horizontal direction to the first distal end portion 72a side of the first side portion 72 and the tangent Lt 3 in the horizontal direction to the second distal end portion 73a side of the second side portion 73 that is closer to the tangent Lt5. In FIG. 7A, the second distal end portion 73a side of the second side portion 73 bites deeper than the first distal end portion 72a side of the first side portion 73. Therefore, the distance CFA is the minimum distance in the height direction between the lowermost part of the upper surface of the bottom portion 74 and the second distal end portion 73a side of the second side portion 73 (the distance between the tangent Lt5 and the tangent Lt3). When the first distal end portion 72a bites (is entangled) into the plurality of core wires 48a as shown in FIG. 7A, "the first distal end portion 72a side of the first side portion 72" may be defined as "the part of the first side portion 72 that bites (is entangled) into the plurality of core wires 48a." Similarly, when the second distal end portion 73a bites (is entangled) into the plurality of core wires 48a as shown in FIG. 7A, "the second distal end portion 73a side of the second side portion 73" may be defined as "the part of the second side portion 73 that bites (is entangled) into the plurality of core wires 48a." When serrations (to be described in detail later) are formed in part of the inner peripheral surface (the surface on the side of the core wires 48a) of the bottom portion 74, the distance CFA is obtained in the section of the part where serrations are not formed. However, when serrations are formed in the whole inner peripheral surface of the bottom portion 74, the distance CFA is obtained in the section of the part where serrations are formed. The distance CFA, although it is not particularly limited, may be, for example, 0.40 mm or less.

The fifth condition is that "the distance CFE is 0 mm or more and 0.25 mm or less." Here, the distance CFE is the distance in the height direction between the tangent Lt 2 in the horizontal direction to the first distal end portion 72a side of the first side portion 72 and the tangent Lt 3 in the horizontal direction to the second distal end portion 73a side of the second side portion 73 (see FIG. 7A). The tangent Lt2 is a tangent that is tangent to the lower end of the first distal end portion 72a side of the first side portion 72 as shown in FIG. 7A). Similarly, the tangent Lt3 is a tangent that is tangent to the lower end of the second distal end portion 73a side of the second side portion 73 as shown in FIG. 7A).

Figure 8:
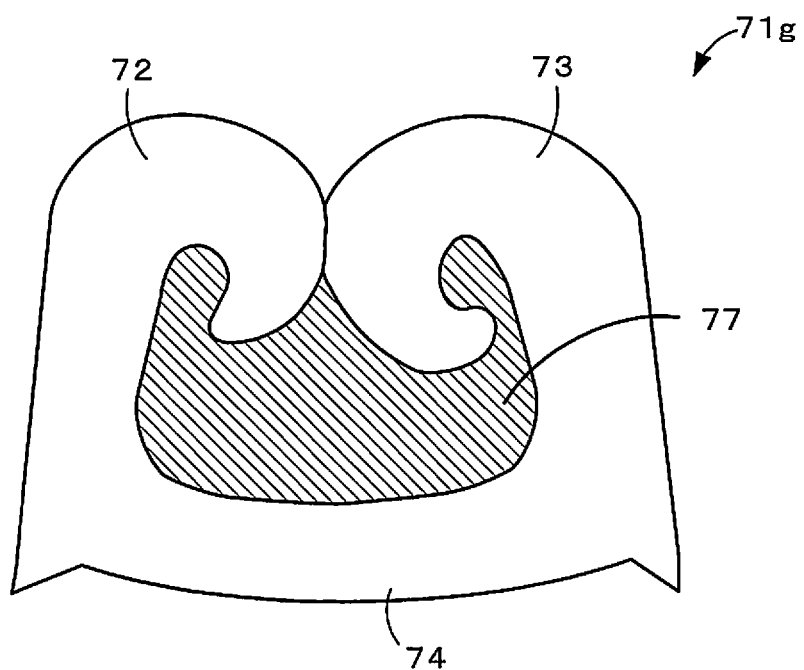
FIG. 8 is an explanatory diagram of a region 77 surrounded by a bottom portion 74, a first side portion 72, and a second side portion 73.

The sixth condition is that "the compression rate CR [%] is 87% or less." Here, the compression rate CR [%]=(the area of the region surrounded by the bottom portion 74, the first side portion 72, and the second side portion 73)/{(the cross-sectional area of each core wire 48a before crimping)×(the number of the crimped core wires 48a)}×100. FIG. 8 is an explanatory diagram of the region 77 surrounded by the bottom portion 74, the first side portion 72, and the second side portion 73. FIG. 8 shows the same section as FIG. 7A. The area of the hatched region 77 shown in FIG. 8 is "the area of the region surrounded by the bottom portion 74, the first side portion 72, and the second side portion 73." The lower limit of compression rate CR is determined by, for example, the material and number of the core wires 48a and the force applied during crimping. The compression rate CR may be, for example, 50% or more.

The seventh condition is that "no cracks are generated in rising parts on the side of the core wires 48a from the bottom portion 74 to the first side portion 72 and the second side portion 73." In FIG. 7A, the rising part 74a is "the rising part on the side of the core wires 48a from the bottom portion 74 to the first side portion 72." The rising part 74b is "the rising part on the side of the core wires 48a from the bottom portion 74 to the second side portion 73."

The eighth condition is that "the burr height Gh of the bottom portion 74 is 0 mm or more and 0.25 mm or less, and the burr is within a region that is closer to the core wires 48a than the lowermost part (the lowermost surface) of the bottom portion 74 in the height direction." The fact that the burr height Gh is 0 mm means that no burr is generated. As described in detail later, when the core wires 48a are crimped by the holding portion 71g, a burr 75 and a burr 76 may be generated at both ends of the bottom portion 74 as shown in FIG. 7A. The heights of the burr 75 and the burr 76 from the bottom portion 74 are referred to as burr heights Gh. When there are a plurality of burrs as in this embodiment, the eighth condition is deemed to be satisfied when the burr heights Gh of the burrs are all within the above range. "The burr is within a region that is closer to the core wires 48a than the lowermost part of the bottom portion 74 in the height direction" means that "there is no burr below a tangent Lt4 that is tangent to the lowermost part of the bottom portion 74 and that is parallel to the horizontal direction." In FIG. 7A, "the burrs 75 and 76 at both ends are within the region that is closer to the core wires 48a than the lowermost part of the bottom portion 74 in the height direction."

The ninth condition is that "the burr widths Gb of the bottom portion 74 are all 0 mm or more and 0.125 mm or less." Here, the burr widths Gb are the widths in the horizontal direction of the burrs 75 and 76 (see FIG. 7A). The fact that the burr width Gb is 0 mm means that no burr is generated. When there are a plurality of burrs as in this embodiment, the ninth condition is deemed to be satisfied when the burr widths Gb of the burrs are all within the above range.

The tenth condition is that "the bottom portion thickness Sb is 0.1875 mm or more." Here, the bottom portion thickness Sb is the thickness in the height direction of the part of contact point P3 between the above tangent Lt4 and the bottom portion 74 (see FIG. 7A). When serrations (to be described in detail later) are formed in part of the inner peripheral surface (the surface on the side of the core wires 48a) of the bottom portion 74, the bottom portion thickness Sb is obtained as the thickness in the section of the part where serrations are not formed. However, when serrations are formed in the whole inner peripheral surface of the bottom portion 74, the bottom portion thickness Sb is obtained as the thickness in the section of the part where serrations are formed. The bottom portion thickness Sb, although it is not particularly limited, may be, for example, 0.30 mm or less.

The holding portion 71g of this embodiment satisfies all of the above-described first to tenth conditions in the section of FIG. 7. In this case, the holding portion 71g can fix the core wires 48a of the lead wire 48 more firmly. In addition, in the section of FIG. 7, it is preferable that the number of spaces between the core wires 48a be small. The smaller the number of spaces, the more hardly the core wires 48a are displaced, and the more firmly the core wires 48a can be fixed. When the first to tenth conditions are all satisfied, the number of spaces is preferably one or less (up to one space is acceptable).

The clamp 90 is made by bending a metal plate as shown in FIG. 2 and FIG. 5, and has an elastic force capable of clamping the first housing 51a and the second housing 51b and pressing them toward each other. When the first housing 51a and the second housing 51b are clamped by this elastic force, the restricting members 56 and 57 of the first housing 51a come into contact with the second housing 51b, and the restricting members 56 and 57 of the second housing 51b come into contact with the first housing 51a. The distance between the first housing 51a and the second housing 51b is thereby fixed. When the clamp 90 clamps the first housing 51a and the second housing 51b with the sensor element 20 and the contact fittings 71 sandwiched between the first housing 51a and the second housing 51b such that the conduction portions 71c of the contact fittings 71 face the first surface electrodes 21a or the second surface electrodes 21b of the sensor element 20, the supporting portions 71b and the conduction portions 71c are elastically deformed by the pressing force from the clamp 90 and clamp and fix the sensor element 20. At this time, since the supporting portions 71b and the conduction portions 71c are elastically deformed, the sensor element 20 can be reliably clamped and fixed by the resulting pressing force. Since the conduction portions 71c are elastically deformed, the electrical contact between the conduction portions 71c and the electrodes 21 can be maintained more reliably.

Figure 9:
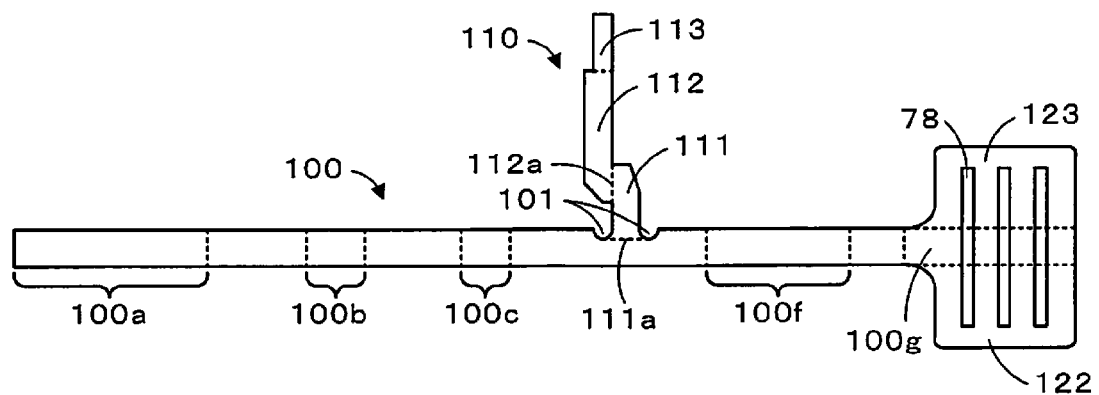
FIG. 9 is an explanatory diagram showing the state of a contact fitting 71 before bending processing.
Figure 10:
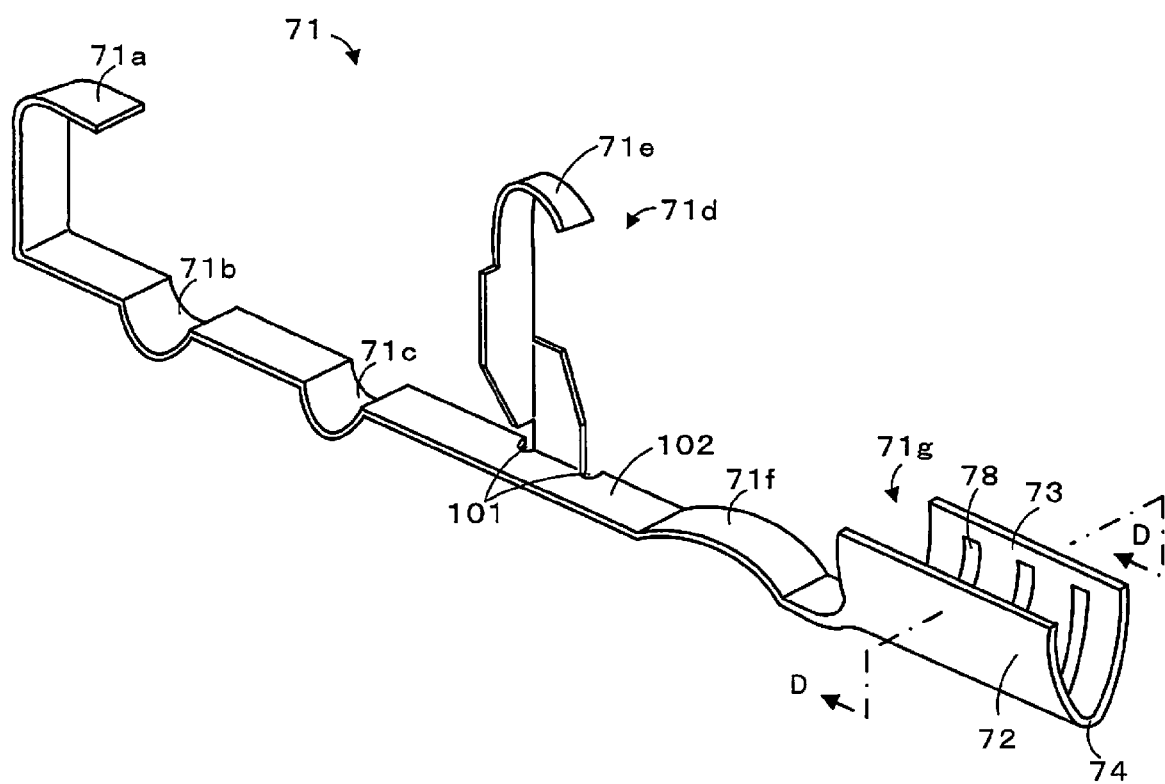
FIG. 10 is a perspective view of the contact fitting 71 after bending processing.
Figure 11:
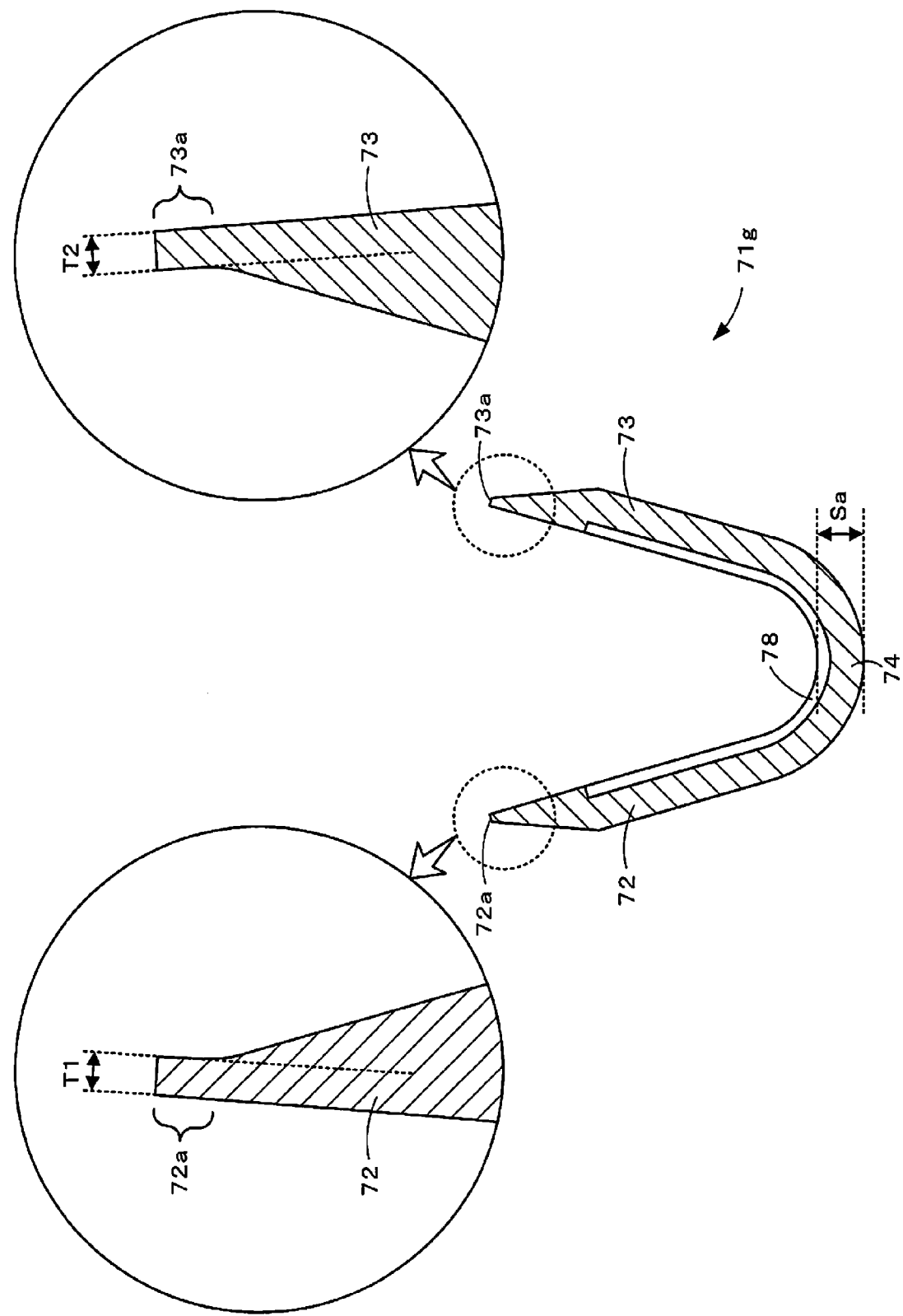
FIG. 11 is a sectional view taken along line D-D of FIG. 10.

Next, a method for manufacturing the contact fitting 71 will be described. The contact fitting 71 is manufactured by punching and bending a metal plat. FIG. 9 is an explanatory diagram showing the state of the contact fitting 71 before bending. FIG. 10 is a perspective view of the contact fitting 71 after bending. FIG. 11 is a sectional view taken along line D-D of FIG. 10. First, as shown in FIG. 9, a metal plate is punched into a shape having a substantially rectangular metal plate portion 100, a metal piece 110 continuous with a long side of the metal plate portion 100, and substantially rectangular metal pieces 122 and 123 continuous with the long sides of a region 100g at one end of the metal plate portion 100. The metal piece 122 is located so as to be continuous with the side of the region 100g opposite to the metal piece 123. Next, serrations 78 are formed in the surfaces of the region 100g and the metal pieces 122 and 123 on the near side of FIG. 9. Although, in this embodiment, as shown, three serrations 78 are formed, the number of serrations 78 is not limited to this, and serrations 78 may not be formed. Next, regions 100a and 100f of the metal plate portion 100 are curved toward the near side of FIG. 9 to form the distal end portion 71a and the curved portion 71f shown in FIG. 4, and regions 100b and 100c are curved so as to protrude toward the far side of FIG. 9 to form the supporting portion 71b and the conduction portion 71c shown in FIG. 4. A region 111 of the metal piece 110 is bent along a straight line 111a toward the near side until it becomes parallel to the direction toward the near side of FIG. 9, a region 112 of the metal piece 110 is bent along a straight line 112a toward the inside of the metal plate portion 100, and a region 113 of the metal piece 110 is curved along the longitudinal direction of the metal plate portion 100 toward the curved portion 71f to form the hook portion 71e. Thus, the metal piece 110 is bent to form the upright portion 71d. As shown in FIG. 9 and FIG. 10, notches 101 having a depth greater than or equal to the thickness of the region 111 are formed in the metal plate portion 100 so that when the region 111 is bent along the straight line 111a, the region 111 is within a region just above the surface 102 of the metal plate portion 100 (see FIG. 10). The metal pieces 122 and 123 are erected toward the near side of FIG. 9 to form the holding portion 71g having a substantially U-shaped cross-section. At this time, the end of each of the metal pieces 122 and 123 on the side opposite to the side continuous with the bottom portion is thinned by compression processing so that the end has a thickness of 70% or less of the thickness of the region 100g. When, as in this embodiment, serrations 78 are formed in part of the region 100g, the compression processing of the end of each of the metal pieces 122 and 123 is performed such that the end has a thickness of 70% or less of the thickness of part of the region 100g where serrations 78 are not formed. However, when serrations 78 are formed in the whole region 100g, the compression processing of the end of each of the metal pieces 122 and 123 is performed such that the end has a thickness of 70% or less of the thickness of part of the region 100g where serrations 78 are formed. In this way, the contact fitting 71 having a three-dimensional shape shown in FIG. 10 and FIG. 11 is manufactured.

The shape of the holding portion 71g of the thus manufactured contact fitting 71 after bending processing, that is, the contact fitting 71 before crimping core wires 48a will be described in detail. In the state before crimping, as described above, the holding portion 71g is formed in a substantially U-shape (see FIG. 10 and FIG. 11). The region 100g in FIG. 9 becomes the bottom portion 74, the metal piece 122 in FIG. 9 becomes the first side portion 72, and the metal piece 123 becomes the second side portion 73. Since the end of each of the metal pieces 122 and 123 in FIG. 9 on the side opposite to the side continuous with the bottom portion is thinned by compression processing, the first distal end portion 72a, which is the end of the first side portion 72 on the side opposite to the side continuous with the bottom portion, is thinned, and the second distal end portion 73a, which is the end of the second side portion 73 on the side opposite to the side continuous with the bottom portion, is thinned (see FIG. 11). The thickness T1 of the first distal end portion 72a and the thickness T2 of the second distal end portion are formed so as to be 70% or less of the thickness of the region 100g in FIG. 9 as described above, and therefore the thicknesses T1 and T2 are both 70% or less of the thickness Sa of the bottom portion 74. In this embodiment, the thicknesses T1 and T2 are both smaller than the diameter of the core wires 48a of the lead wire 48 before crimping. The smaller the thicknesses T1 and T2, the more easily the first distal end portion 72a and the second distal end portion 73a bite into the plurality of core wires 48a. However, from the manufacturing viewpoint and the viewpoint of the strength of the first distal end portion 72a and the second distal end portion 73a, the thicknesses T1 and T2 are preferably 40% or more of the thickness of the bottom portion. When, as shown in FIG. 10, serrations 78 are formed in part of the inner peripheral surface (the upper surface in FIG. 11) of the bottom portion 74, the thickness Sa is obtained as the thickness in the section of the part where serrations 78 are not formed (see FIG. 11). However, when serrations 78 are formed in the whole inner peripheral surface of the bottom portion 74, the bottom portion thickness Sa is obtained as the thickness in the section of the part where serrations 78 are formed. Although, in this embodiment, as shown in FIG. 11, the first side portion 72 has a shape that becomes gradually thinner toward the first distal end portion 72a, the first side portion 72 may have another shape as long as the thickness T1 of the first distal end portion 72a is 70% or less of the thickness Sa. The same is true on the second side portion 73. The thickness Sa, although it is not particularly limited, may be, for example, 0.10 mm to 0.40 mm. The diameter of core wires 48a before crimping is, for example, 0.126 mm to 0.623 mm, and the number of core wires 48a in a lead wire 48 is, for example, 2 to 40.

Next, a method for manufacturing a gas sensor 10 employing contact fittings 71 after bending processing shown in FIG. 10 and FIG. 11 will be described. First, a main fitting 41 and an inner cylinder 42 are coaxially joined together by welding, the inside thereof is filled with a ceramic supporter 43a, ceramic powder 44a, a ceramic supporter 43b, ceramic powder 44b, and a ceramic supporter 43c in this order from the main fitting 41 side, and then a metal ring 45 is inserted. Next, a sensor element 20 is prepared, and the sensor element 20 is passed through the ceramic supporter 43c, ceramic powder 44b, ceramic supporter 43b, ceramic powder 44a, and ceramic supporter 43a in this order from the metal ring 45 side. Holes through which the sensor element 20 can be passed are preliminarily formed in the ceramic supporters 43a to 43c, the ceramic powder 44a and 44b, and the metal ring 45. The metal ring 45 and the main fitting 41 are pressed toward each other to compress the ceramic powder 44a and 44b. In that state, the inner cylinder 42 on the outer side (the upper side in FIG. 1) of the metal ring 45 is reduced in diameter by crimping processing. Further, part of the inner cylinder 42 in which the ceramic powder 44b is disposed is reduced in diameter by crimping processing. Thus, a primary assembly including the main fitting 41 and the sensor element 20 is obtained.

After the primary assembly is obtained, an inner protective cover 31 and an outer protective cover 32 are attached to the main fitting 41 by welding to form a protective cover 30, and an outer cylinder 46 is attached to the main fitting 41 by welding. Next, a plurality of (eight in this embodiment) contact fittings 71 after bending shown in FIG. 10 and FIG. 11 are prepared, and a plurality of (eight in this embodiment) lead wires 48 and a rubber plug 47 having a through-hole 47a formed therein are prepared. Next, the plurality of lead wires 48 are passed through the through-hole 47a of the rubber plug 47, then the core wires 48a of the plurality of lead wire 48 are surrounded and crimped with the holding portions 71g of the contact fittings 71, and the contact fittings 71 and the lead wires 48 are thereby electrically connected. The eight contact fittings 71 and the eight lead wires 48 are each crimped, and eight crimp bodies 80 each including a contact fitting 71 and a lead wire 48 connected to each other are thereby manufactured.

Figure 12:
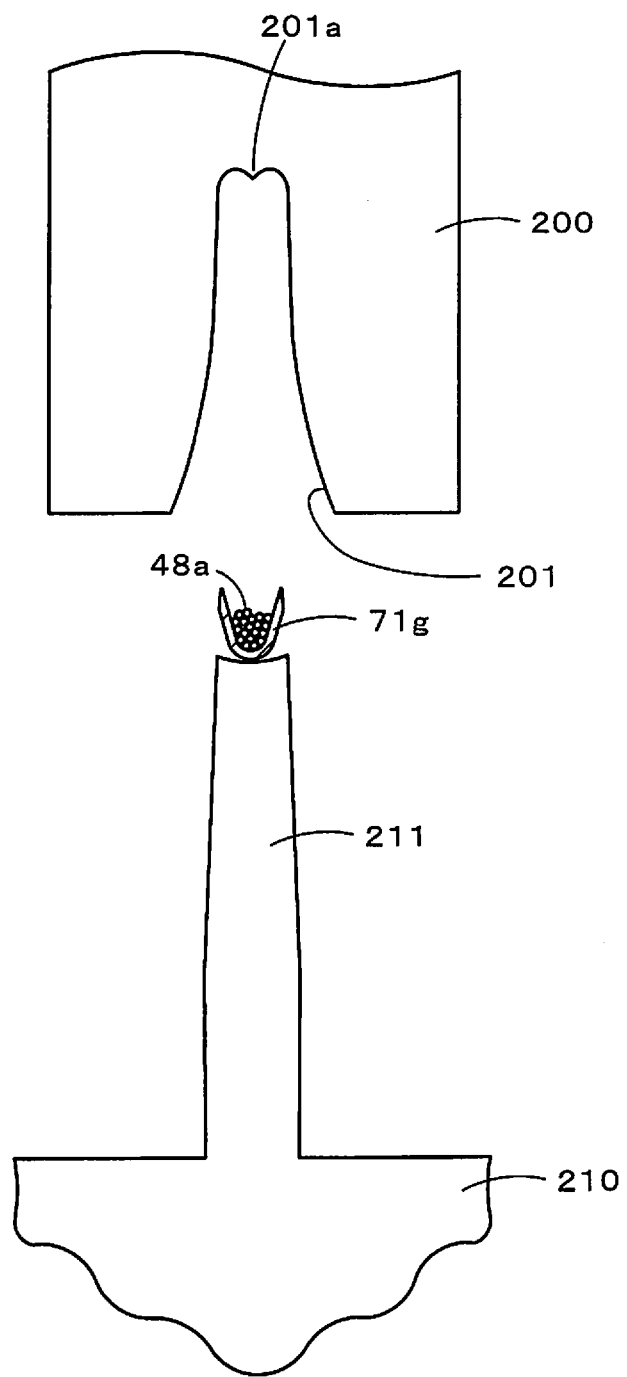
FIG. 12 is an explanatory diagram showing a state in which a holding portion 71g and core wires 48a are disposed between a crimper 200 and an anvil 210.
Figure 13A:
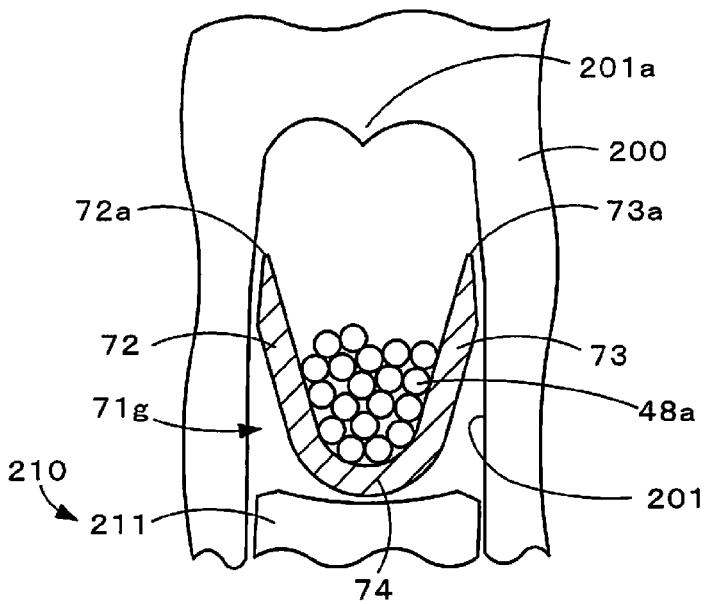
FIG. 13 is an explanatory diagram showing a state in which the holding portion 71g and the core wires 48a are crimped to form a crimp body 80.
Figure 13B:
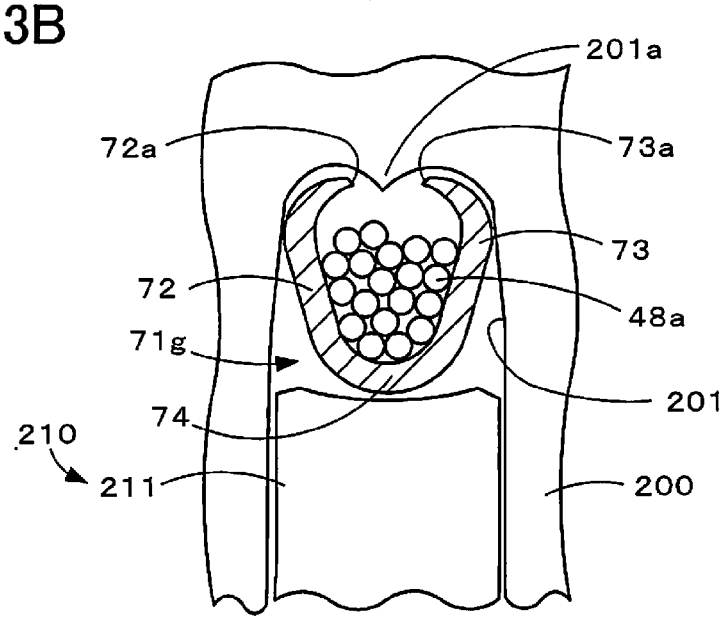
Figure 13C:
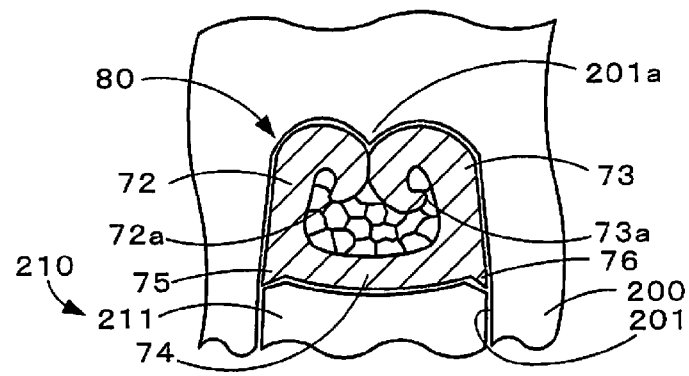

The manufacturing of a crimp body 80 including a contact fitting 71 and a lead wire 48 will be described in detail. FIG. 12 is an explanatory diagram showing a state where a holding portion 71g and core wires 48a are disposed between a crimper 200 and an anvil 210. FIG. 13 is an explanatory diagram showing a state where the holding portion 71g and the core wires 48a are crimped to form a crimp body 80. First, the contact fitting 71 shown in FIGS. 10 and 11 and a lead wire 48 having a plurality of core wires 48a are prepared. An anvil 210 and a crimper 200 are prepared. As shown in FIG. 12, the anvil 210 has a protruding portion 211 protruding upward in the figure. The crimper 200 has a recessed portion 201 that is open downward in the figure and into which the protruding portion 211 can be inserted. The bottom of the recessed portion 201 (the upper end of the recessed portion 201 in FIG. 12) has a protrusion 201a formed in the center thereof, and is formed in a substantially M-shape that curves from both sides of the recessed portion 201 toward the protrusion 201a in the center. Next, the holding portion 71g of the contact fitting 71 is placed on the end face of the protruding portion 211 of the anvil 210, and the plurality of core wires 48a of the lead wire 48 are placed on the inner peripheral surface of the bottom portion 74 (FIG. 12). Next, the crimper 200 is moved toward the anvil 210, the holding portion 71g, the core wires 48a, and the protruding portion 211 are inserted into the inside of the recessed portion 201, and the crimper 200 is moved further toward the anvil 210 (FIG. 13A). Thus, the first distal end portion 72a of the first side portion 72 and the second distal end portion 73a of the second side portion 73, which are located closest to the crimper 200 in the holding portion 71g, approach the bottom of the recessed portion 201. The crimper 200 is moved further toward the anvil 210, the first distal end portion 72a and the second distal end portion 73a first come into contact with the bottom of the recessed portion 201, and the first distal end portion 72a and the second distal end portion 73a move along the curvature of the bottom of the recessed portion 201 so as to approach each other. The first side portion 72 and the second side portion 73 are thereby curved such that the first distal end portion 72a and the second distal end portion 73a face toward the bottom portion 74 (FIG. 13B). The crimper 200 is moved further toward the anvil 210, and the crimper 200 and the anvil 210 are pressed toward each other. The first distal end portion 72a and the second distal end portion 73a thereby bite into the plurality of core wires 48a, and the plurality of core wires 48a are surrounded and crimped with the bottom portion 74, the first side portion 72, and the second side portion 73 (FIG. 13C). Thus, a crimp body 80 is manufactured. At this time, by the force pressing the crimper 200 and the anvil 210 toward each other, parts of the member of the holding portion 71g may be pressed into the spaces between the protruding portion 211 and both side surfaces of the recessed portion 201 to form burrs 75 and 76 on the bottom portion 74 as shown in FIG. 13C.

Here, as described above, the thicknesses T1 and T2 of the first distal end portion 72a and the second distal end portion 73a in the state before crimping are both 70% or less of the thickness Sa of the bottom portion 74. Therefore, the first distal end portion 72a and the second distal end portion 73a easily bite into the plurality of core wires 48a, and the core wires 48a of the lead wire 48 can be fixed more firmly with the bottom portion 74, the first side portion 72, and the second side portion 73. Since the first side portion 72 and the second side portion 73 have a shape that becomes gradually thinner toward the distal end portion 72a, 73a as shown in FIG. 11, also owing to this shape, the first distal end portion 72a and the second distal end portion 73a easily bite into the plurality of core wires 48a. Since the first distal end portion 72a and the second distal end portion 73a easily bite into the plurality of core wires 48a, a crimp body that satisfies the above first to tenth conditions described with reference to FIG. 7 and FIG. 8 when the holding portion 71g is viewed in a section perpendicular to the axial direction of the core wires 48a can be made relatively easily. For example, the curved shape of the bottom of the recessed portion 201, the protrusion height of the protrusion 201a, the load when the crimper 200 and the anvil 210 are pressed toward each other, and the like can be preliminarily determined, for example, by experiments such that the first distal end portion 72a and the second distal end portion 73a can bite into the plurality of core wires 48a more easily and such that the first to tenth conditions can be easily satisfied.

After the crimp body 80 is manufactured, the above-described housing 51 including a first housing 51a and a second housing 51b, and a clamp 90 are prepared, and the sensor element 20 is sandwiched between the first housing 51a and the second housing 51b, with each of the first housing 51a and the second housing 51b holding four contact fittings 71 of crimp bodies 80. Thus, the sensor element 20 and the plurality of contact fittings 71 are sandwiched between the first housing 51a and the second housing 51b. In each of the contact fittings 71, as described with reference to FIG. 4 to FIG. 6, the supporting portion 71b is in contact with the surface of the sensor element 20, and the conduction portion 71c is in contact with the electrode 21. Then, in this state, the first housing 51a and the second housing 51b are clamped and fixed by the clamp 90. Thus, the clamp 90 is brought into a state in which it presses the first housing 51a and the second housing 51b toward each other. By this pressing force, the contact fittings 71 are pressed toward the sensor element 20, the supporting portions 71b come into contact with the surface of the sensor element 20, the conduction portions 71c come into contact with and are electrically connected to the electrodes 21 of the sensor element 20, and the supporting portions 71b and the conduction portions 71c are elastically deformed and press the sensor element 20. After that, the rubber plug 47 is inserted into the outer cylinder 46 through the open end 46a, the outer cylinder 46 and the rubber plug 47 are reduced in diameter by crimping, and the rubber plug 47 is fixed to the outer cylinder 46. In this way, a gas sensor 10 can be manufactured.

Here, the correspondence relationship between the components of this embodiment and the components of the present invention will be clarified. The contact fitting 71 of this embodiment corresponds to the crimp terminal of the present invention, the bottom portion 74 corresponds to the bottom portion, the first side portion 72 corresponds to the first side portion, the second side portion 73 corresponds to the second side portion, the holding portion 71g corresponds to the holding portion, the first distal end portion 72a corresponds to the first distal end portion, and the second distal end portion 73a corresponds to the second distal end portion.

According to the embodiment described above in detail, in the contact fitting 71 in a state before crimping, the thickness T1 of the first distal end portion 72a is 70% or less of the thickness Sa of the bottom portion 74, and the thickness T2 of the second distal end portion 73a is 70% or less of the thickness Sa of the bottom portion 74. Therefore, when the holding portion 71g crimps the plurality of core wires 48a, the first distal end portion 72a and the second distal end portion 73a easily bite into the plurality of core wires 48a. Therefore, the core wires 48a of the lead wire 48 can be fixed more firmly with the bottom portion 74, the first side portion 72, and the second side portion 73. By firmly fixing the core wires 48a with the holding portion 71g, the lead wire 48 can be prevented from easily coming off after crimping. The adhesion between the contact fitting 71 and the core wires 48a and the adhesion between the core wires 48a are made sufficient, and the contact resistance in the crimp part can be prevented from varying.

Since the thicknesses T1 and T2 are both smaller than the diameter of the core wires 48a of the lead wire 48 before crimping, the first distal end portion 72a and the second distal end portion 73a bite into the plurality of core wires 48a more easily.

Since the first distal end portion 72a and the second distal end portion 73a are formed by compression processing, the strength of the first distal end portion 72a and the second distal end portion 73a can be made high compared to the case where the first distal end portion 72a and the second distal end portion 73a are thinned, for example, by polishing or grinding.

The crimp body 80 includes a lead wire 48 having a plurality of core wires 48a, and a contact fitting 71. The first side portion 72 and the second side portion 73 are curved such that the first distal end portion 72a and the second distal end portion 73a face the bottom portion 74, and the holding portion 71g of the contact fitting 71 thereby surrounds and crimps the plurality of core wires 48a with the bottom portion 74, the first side portion 72, and the second side portion 73. When the holding portion 71g is viewed in a section perpendicular to the axial direction of the core wires 48a, the crimp body 80 satisfies the first condition (the crimp height CH is 1.20±0.05 mm and the crimp width CW is 1.66±0.05 mm). Therefore, the holding portion 71g is sufficiently compressed in the height direction of the section, and the core wires 48a can be fixed more firmly.

When the holding portion 71g is viewed in a section perpendicular to the axial direction of the core wires 48a, the crimp body 80 satisfies the second condition (the height Ha is 0.15 mm or more). Therefore, the contact (crimping) between the first side portion 72 and the second side portion 73 is made sufficient, and the core wires 48a can be fixed more firmly.

When the holding portion 71g is viewed in a section perpendicular to the axial direction of the core wires 48a, the crimp body 80 satisfies the third condition (the angle $\alpha$ is 0° or more and 30° or less). Therefore, the first side portion 72 and the second side portion 73 can crimp the core wires 48a in a balanced manner, and the core wires 48a can be fixed more firmly.

When the holding portion 71g is viewed in a section perpendicular to the axial direction of the core wires 48a, the crimp body 80 satisfies the fourth condition (the distance CFA is 0.125 mm or more). When the distance CFA is smaller than 0.125 mm, the distance between at least one of the first distal end portion 72a side of the first side portion 72 and the second distal end portion 73a side of the second side portion 73 and the bottom portion is small, and some of the core wires 48a may be excessively crushed. This can be prevented by making the distance CFA 0.125 mm or more. That is, by making the distance CFA 0.125 mm or more, the plurality of core wires 48a can be crimped in a balanced manner, and the core wires 48a can be fixed more firmly.

When the holding portion 71g is viewed in a section perpendicular to the axial direction of the core wires 48a, the crimp body 80 satisfies the fifth condition (the distance CFE is 0 mm or more and 0.25 mm or less). Therefore, the first side portion 72 and the second side portion 73 can crimp the core wires 48a in a balanced manner, and the core wires 48a can be fixed more firmly.

When the holding portion 71g is viewed in a section perpendicular to the axial direction of the core wires 48a, the crimp body 80 satisfies the sixth condition (the compression rate CR [%] is 87% or less). Therefore, the holding portion 71g compresses the core wires 48a sufficiently, and the core wires 48a can be fixed more firmly.

When the holding portion 71g is viewed in a section perpendicular to the axial direction of the core wires 48a, the crimp body 80 satisfies the seventh condition (no cracks are generated in rising parts 74a and 74b). Therefore, compared to a case where cracks are generated, the strength of the holding portion 71g is high, and therefore the core wires 48a can be fixed more firmly.

When the holding portion 71g is viewed in a section perpendicular to the axial direction of the core wires 48a, the crimp body 80 satisfies the eighth condition (the burr heights Gh of the burrs 75 and 76 are both 0 mm or more and 0.25 mm or less, and the burrs 75 and 76 are within a region that is closer to the core wires 48a than the lowermost part of the bottom portion 74 in the height direction). If the burrs 75 and 76 are large, the percentage of part of the member forming the bottom portion 74, the first side portion 72, and the second side portion 73 that does not affect the fixing of the core wires 48a increases, and therefore the fixing of the core wires 48a is prone to be insufficient. By satisfying the eighth condition, such an effect of the burrs 75 and 76 can be made relatively small, and the core wires 48a can be fixed more firmly.

When the holding portion 71g is viewed in a section perpendicular to the axial direction of the core wires 48a, the crimp body 80 satisfies the ninth condition (the burr widths Gb of the burrs 75 and 76 are both 0 mm or more and 0.125 mm or less). Therefore, the above-described effect of the burrs 75 and 76 is relatively small, and the core wires 48a can be fixed more firmly.

When the holding portion 71g is viewed in a section perpendicular to the axial direction of the core wires 48a, the crimp body 80 satisfies the tenth condition (the bottom portion thickness Sb is 0.1875 mm or more). Therefore, the strength of the bottom portion 74 is higher, and therefore the core wires 48a can be fixed more firmly.

A crimp body 80 is manufactured by using a contact fitting 71 in which the thicknesses T1 and T2 are 70% or less of the thickness Sa of the bottom portion 74 in a state before crimping, curving the first side portion 72 and the second side portion 73 such that the first distal end portion 72a and the second distal end portion 73a face the bottom portion 74, and surrounding and crimping a plurality of core wires 48a with the bottom portion 74, the first side portion 72, and the second side portion 73. Therefore, the first distal end portion 72a and the second distal end portion 73a easily bite into the plurality of core wires 48a, and the core wires 48a of the lead wire 48 can be fixed more firmly with the bottom portion 74, the first side portion 72, and the second side portion 73.

The present invention is not limited to the above-described embodiment, and can be implemented in various forms as long as they fall within the technical scope of the present invention.

For example, although in the above-described embodiment, in the contact fitting 71 before crimping, the thicknesses T1 and T2 are smaller than the diameter of the core wires 48a of the lead wire 48 to be crimped, the present invention is not limited to this, and the thicknesses T1 and T2 may be larger than the diameter of the core wires 48a. However, in order for the first distal end portion 72a and the second distal end portion 73a to easily bite into the plurality of core wires 48a, the thicknesses T1 and T2 are preferably smaller than the diameter of the core wires 48a of the lead wire 48 to be crimped. In a state after the crimping of the core wires 48a by the holding portion 71g, the thicknesses of the first distal end portion 72a and the second distal end portion 73a may change due to crimping. Therefore, the thicknesses of the first distal end portion 72a and the second distal end portion 73a after crimping do not necessarily have to be smaller than the diameter of the core wires 48a.

In the above-described embodiment, in the contact fitting 71 before crimping, the thicknesses T1 and T2 are 70% or less of the thickness Sa of the bottom portion 74. However, also in the contact fittings 71 after crimping, the thicknesses of the first distal end portion 72a and the second distal end portion 73a may be 70% or less of the thickness Sa of the bottom portion 74. As described above, owing to crimping, the thicknesses of the first distal end portion 72a and the second distal end portion 73a may change, and the thickness of the bottom portion 74 may change. Therefore, the thicknesses of the first distal end portion 72a and the second distal end portion 73a after crimping do not necessarily have to be 70% or less of the thickness Sb of the bottom portion 74 after crimping. The ends of the holding portion 71g of the contact fitting 71 after crimping in the axial direction of the core wires 48a (the left and right ends of 71g in FIG. 4) may have a shape such that the holding portion 71g and the core wires 48a are not completely crimped compared to the other part (bell-mouth shape). In this bell-mouthed part, compared to the other part, the change in the thickness of the holding portion 71g due to crimping is small. Therefore, when, in a section of the bell-mouthed part perpendicular to the axial direction of the core wires 48a, the thicknesses of the first distal end portion 72a and the second distal end portion 73a are 70% or less of the thickness Sa of the bottom portion 74, it can be deemed that, in the contact fitting 71 before crimping, the thicknesses T1 and T2 are 70% or less of the thickness Sa of the bottom portion 74.

In the above-described embodiment, the first distal end portion 72a and the second distal end portion 73a are thinned by compression processing. However, the present invention is not limited to compression processing, and the first distal end portion 72a and the second distal end portion 73a may be thinned by another processing method such as polishing or grinding. When the first distal end portion 72a and the second distal end portion 73a are thinned by processing not limited to compression processing, the thicknesses of the first distal end portion 72a and the second distal end portion 73a after processing may be 70% or less of the thicknesses before processing. Not only the first distal end portion 72a and the second distal end portion 73a but also the whole first side portion 72 and the whole second side portion 73 may be thinned.

In the above-described embodiment, when the holding portion 71g is viewed in a section perpendicular to the axial direction of the core wires 48a, the crimp body 80 satisfies all of the first to tenth conditions. However, the present invention is not limited to this. If at least one of the first to tenth conditions are satisfied, the core wires 48a can be fixed more firmly. However, the larger the number of satisfied conditions, the more firmly the core wires 48a can be fixed. It is only necessary to satisfy at least one of the first to tenth conditions in a section of the holding portion 71g. However, it is preferable that at least one of the first to tenth conditions be satisfied in a plurality of sections of the holding portion 71g, and it is more preferable that at least one of the first to tenth conditions be satisfied in any section of the holding portion 71g. However, when serrations are formed in part of the inner peripheral surface of the bottom portion 74, it is only necessary to satisfy at least one of the first to tenth conditions in a section of part of the holding portion 71g where serrations are not formed, it is preferable that at least one of the first to tenth conditions be satisfied in a plurality of sections, and it is more preferable that at least one of the first to tenth conditions be satisfied in any section. Similarly, when the ends of the holding portion 71g after crimping in the axial direction of the core wires 48a are bell-mouthed, it is only necessary to satisfy at least one of the first to tenth conditions in a section of part of the holding portion 71g other than the bell-mouthed parts, it is preferable that at least one of the first to tenth conditions be satisfied in a plurality of sections, and it is more preferable that at least one of the first to tenth conditions be satisfied in any section. If, in the contact fitting 71 before crimping, the thicknesses T1 and T2 are 70% or less of the thickness Sa of the bottom portion 74, the crimp body 80 after crimping may not satisfy any one of the first to tenth conditions. Also in this case, the first distal end portion 72a and the second distal end portion 73a easily bite into the plurality of core wires 48a, and therefore the core wires 48a can be fixed more firmly.

Although, in the above-described embodiment, in the contact fitting 71 before crimping, the thicknesses T1 and T2 are 70% or less of the thickness Sa of the bottom portion 74, the shape of the contact fitting 71 before crimping is not limited to this as long as the first to tenth conditions are satisfied in the crimp body 80 after crimping.

EXAMPLES

Example 1

Figure 14:
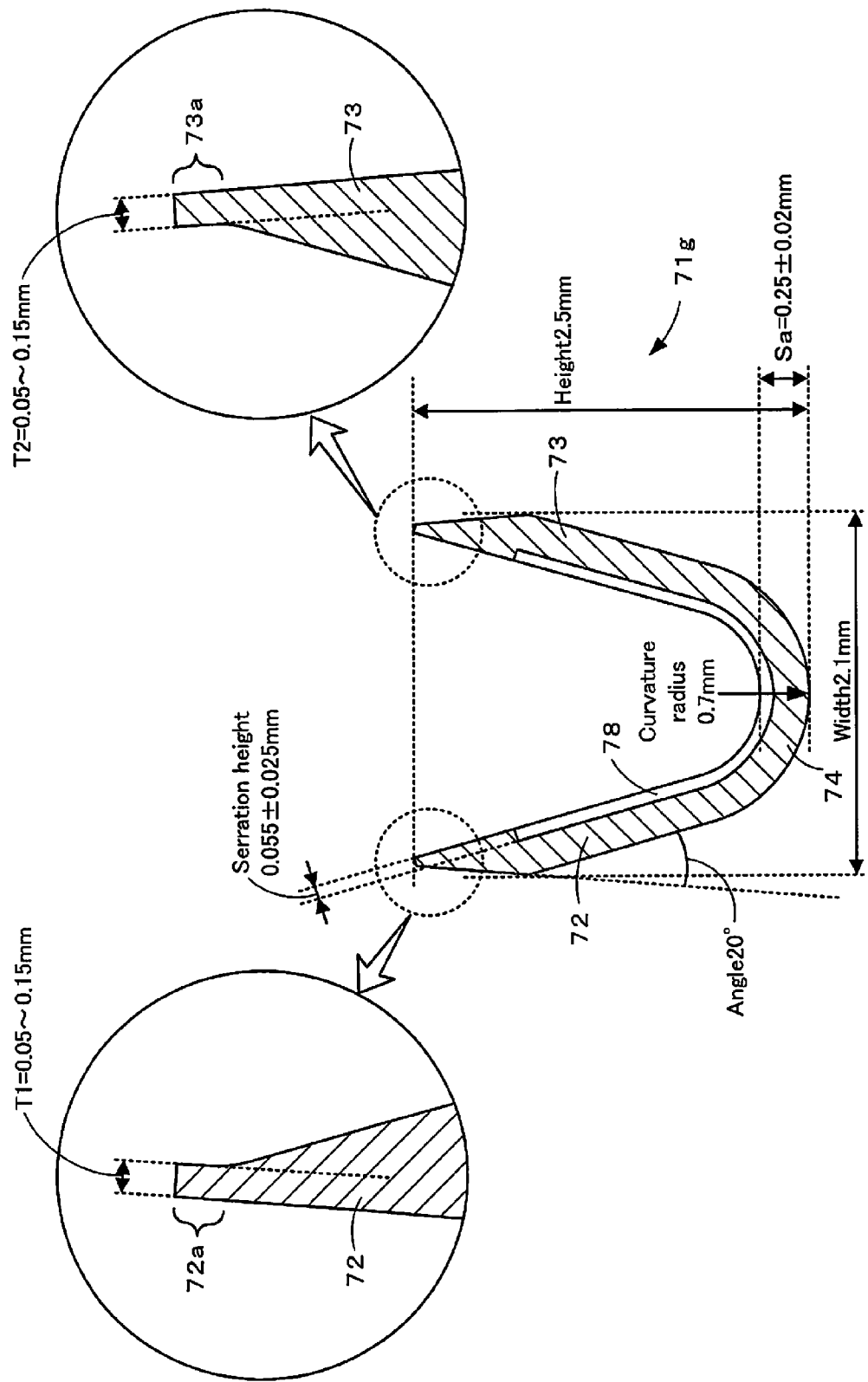
FIG. 14 is an explanatory diagram showing the section size of a holding portion 71g of a contact fitting 71 of Example 1.

The contact fitting 71 shown in FIGS. 10 and 11 was made by the above-described manufacturing method, and is designated as Example 1. The contact fitting 71 of Example 1 is 0.7 mm in width, 0.2 mm in thickness, and 22 mm in length. FIG. 14 is an explanatory diagram showing the dimensions of a section of the holding portion 71g of the contact fitting 71 of Example 1. As shown in FIG. 14, the holding portion 71g of Example 1 was 2.1 mm in width, and 2.5 mm in height, the curvature radius of the outer peripheral surface of the bottom portion 74 was 0.7 mm, the thickness Sa of the bottom portion 74 was 0.25±0.02 mm, the serration height was 0.055±0.025 mm, the angle of parts of the first side portion 72 and the second side portion that become gradually thinner toward the distal end portions 72a and 73a was 20°, and the thicknesses T1 and T2 of the first distal end portion 72a and the second distal end portion 73a were 0.05 or more and 0.15 mm or less. The contact fitting 71 was made of SUS304.

Example 2

Figure 15:
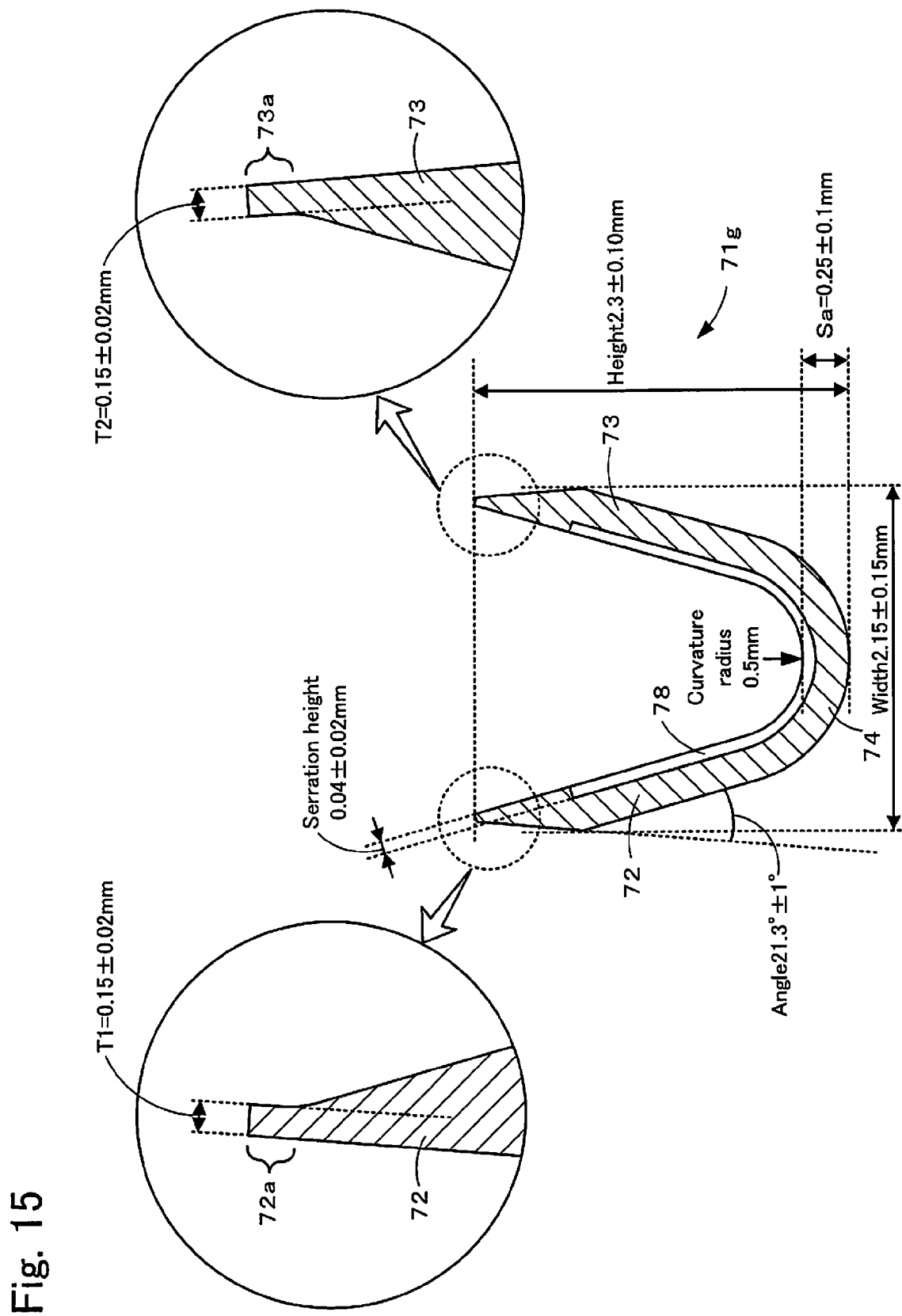
FIG. 15 is an explanatory diagram showing the section size of a holding portion 71g of a contact fitting 71 of Example 2.

A contact fitting 71 that was the same as Example 1 except that the dimensions of the holding portion 71g were changed was made, and is designated as Example 2. FIG. 15 is an explanatory diagram showing the dimensions of a section of the holding portion 71g of the contact fitting 71 of Example 2. As shown in FIG. 15, the holding portion 71g of Example 2 was 2.15±0.15 mm in width, and 2.3±0.10 mm in height, the curvature radius of the inner peripheral surface of the bottom portion 74 was 0.5 mm, the thickness Sa of the bottom portion 74 was 0.25±0.1 mm, the serration height was 0.04±0.02 mm, the angle of parts of the first side portion 72 and the second side portion that become gradually thinner toward the distal end portions 72a and 73a was 21.3°±1°, and the thicknesses T1 and T2 of the first distal end portion 72a and the second distal end portion 73a were 0.15±0.02 mm.

As can be seen from FIG. 14 and FIG. 15, in both Example 1 and Example 2, the thicknesses T1 and T2 of the first distal end portion 72a and the second distal end portion 73a are 70% or less of the thickness Sa of the bottom portion 74. More specifically, in Example 1, the thicknesses T1 and T2 are about 20% to about 60% of the thickness Sa of the bottom portion 74. In Example 2, the thicknesses T1 and T2 are about 60% of the thickness Sa of the bottom portion 74.

[Making of Crimp Body]

Five contact fittings 71 of Example 1 described above and five contact fittings 71 of Example 2 described above were made, and core wires 48a of lead wires 48 were crimped with holding portions 71g by the above-described method to make crimp bodies 80 of Examples 1 and 2. The lead wires 48 used each included 19 core wires 48a that were 0.2 mm in diameter. The load when pressing the crimper 200 and the anvil 210 toward each other was such that the maximum pressing load was within a range of 450 kg±4.0%. The made crimp bodies 80 were cut perpendicularly to the axial direction of the core wires 48a, and it was checked whether or not the sections satisfy the first to tenth conditions. The cutting of the crimp bodies 80 and the observation of the sections were performed using a terminal section cut monitor CS-04PC manufactured by True Soltec Co., Ltd. The results are shown in Table 1. In Table 1, each example was graded as good (O) when all of the five satisfied each condition.

TABLE 1

| | Condition | | Example 1 | | | | Example 2 | | | |
|---|---|---|---|---|---|---|---|---|---|---|
| | | | Average | Maximum | Minimum | Grade | Average | Maximum | Minimum | Grade |
| The first condition | Crimp height CH[mm] | 1.20 ± 00.05 | 1.23 | 1.25 | 1.20 | ○ | 1.19 | 1.20 | 1.19 | ○ |
| | Crimp width CW[mm] | 1.66 ± 00.05 | 1.66 | 1.67 | 1.64 | ○ | 1.67 | 1.67 | 1.66 | ○ |
| The second condition | Height Ha[mm] | ≥0.15 | 0.24 | 0.26 | 0.22 | ○ | 0.20 | 0.20 | 0.20 | ○ |
| The third condition | Angle α [°] | 0~30 | 6.31 | 8.46 | 4.26 | ○ | 3.08 | 5.35 | 0.01 | ○ |
| The fourth condition | Distance CFA[mm] | ≥0.125 | 0.31 | 0.38 | 0.27 | ○ | 0.49 | 0.50 | 0.46 | ○ |
| The fifth condition | Distance CFE[mm] | 0~0.25 | 0.07 | 0.14 | 0.02 | ○ | 0.01 | 0.01 | 0.00 | ○ |
| The sixth condition | Compression rate CR[%] | ≤87 | 57 | 61 | 55 | ○ | 71 | 74 | 67 | ○ |
| The seventh condition | Rising part | No cracks | — | — | — | ○ | — | — | — | ○ |
| The eighth condition | Burr height Gh[mm] | 0~0.25 | 0.02 | 0.04 | 0.00 | ○ | — | — | — | — |
| | Burr position | Closer to core wires than the lowermost part | — | — | — | ○ | — | — | — | — |
| The ninth condition | Burr width Gb[mm] | 0~0.125 | 0.05 | 0.06 | 0.04 | ○ | — | — | — | — |
| The tenth condition | Bottom portion thickness Sb[mm] | ≥0.1875 | 0.24 | 0.26 | 0.22 | ○ | 0.30 | 0.56 | 0.22 | ○ |

As can be seen from Table 1, Example 1 satisfied all of the first to tenth conditions. Although burrs were not measured on Example 2, Example 2 satisfied the first to seventh conditions and the tenth condition. From this, it was found that a crimp body 80 that satisfies the first to tenth conditions can be made relatively easily by making the thicknesses T1 and T2 of the first distal end portion 72a and the second distal end portion 73a 70% of the thickness Sa of the bottom portion 74.

The resistance to pulling (tensile strength) of the lead wire 48 and the uniformity in the contact resistance between the holding portion 71g and the core wires 48a were measured on the crimp bodies 80 of Examples 1 and 2, and it was confirmed that, compared to a crimp body that does not satisfy any one of conditions 1 to 10, the crimp bodies 80 of Examples 1 and 2 can yield good results.

What is claimed is:

1. A crimp body comprising:
   a lead wire having a plurality of core wires; and
   a crimp terminal comprising a holding portion including a bottom portion, a curved first side portion continuous with a first side of the bottom portion, and a curved second side portion continuous with a second side of the bottom portion, the second side being opposite to the first side,
   the first side portion and the second side portion being curved such that a first distal end portion of the first side portion faces the bottom portion and a second distal end portion of the second side portion faces the bottom portion, and the holding portion surrounding and crimping the plurality of core wires with the bottom portion, the first side portion, and the second side portion, and
   when the holding portion is viewed in a section perpendicular to an axial direction of the core wires, in the section, horizontal direction being defined as the direction of a tangent to the curved part of the first side portion and the curved part of the second side portion, height direction being defined as the direction perpendicular to the horizontal direction, a crimp height that is the height from a bottom surface of the bottom portion to the tangent is 1.20±0.05 mm and a crimp width that is the width in the horizontal direction of the holding portion is 1.66±0.05 mm.

2. The crimp body according to claim 1, wherein
   in the section, a height that is the distance in the height direction of the contact part between the first side portion and the second side portion is 0.15 mm or more.

3. The crimp body according to claim 1, wherein
   in the section, an angle that is the angle between the contact part between the first side portion and the second side portion and the height direction is 0° or more and 30° or less.

4. The crimp body according to claim 1, wherein
   in the section, a distance that is the minimum distance in the height direction between a lowermost part of a surface of the bottom portion on the side of the core wires, and a first distal end portion side of the first side portion and a second distal end portion side of the second side portion is 0.125 mm or more.

5. The crimp body according to claim 1, wherein
   in the section, a distance that is the distance in the height direction between a tangent in the horizontal direction to a first distal end portion side of the first side portion and a tangent in the horizontal direction to a second distal end portion side of the second side portion is 0 mm or more and 0.25 mm or less.

6. The crimp body according to claim 1, wherein
   in the section, when a compression rate =(the area of the region surrounded by the bottom portion, the first side portion, and the second side portion) / {(the cross-sectional area of each core wire before crimping) ×(the number of the crimped core wires)}×100, the compression rate is 87% or less.

7. The crimp body according to claim 1, wherein
   the holding portion includes first and second rising parts, the first and second rising parts being disposed on the side of the core wires from the bottom portion to the first side portion and the second side portion, respectively, and, in the section, the rising parts are configured such that no cracks are generated therein.

8. The crimp body according to claim 1, wherein
   in the section, the bottom portion includes a burr, and a height of the burr is 0 mm or more and 0.25 mm or less, and the burr is within a region that is closer to the core wires than a lowermost part of the bottom portion in the height direction.

9. The crimp body according to claim 1, wherein
in the section, the bottom portion includes a burr, and a width of the burr is 0 mm or more and 0.125 mm or less.

10. The crimp body according to claim 1, wherein
in the section, a thickness of a bottom portion is 0.1875 mm or more.

11. A method for manufacturing a crimp body including a crimp terminal including a holding portion including a bottom portion, a first side portion continuous with a first side of the bottom portion, and a second side portion continuous with a second side of the bottom portion, the second side being opposite to the first side, the first side portion having a first side continuous with the first side of the bottom portion, a second side opposite the first side of the first side portion, and a first distal end portion disposed at an end on the second side of the first side portion, and the first distal end portion having a thickness 70% or less of a thickness of the bottom portion, and wherein the second side portion having a first side continuous with the bottom portion, a second side opposite the side of the second side portion, and a second distal end portion disposed at an end on the first side of the second side portion, and the second distal end portion having a thickness 70% or less of the thickness of the bottom portion, the method comprising:
preparing the crimp terminal and a lead wire having a plurality of core wires; and
surrounding and crimping the plurality of core wires with the bottom portion, the first side portion, and the second side portion by curving the first side portion and the second side portion such that the first distal end portion and the second distal end portion face the bottom portion, and the holding portion when viewed in a section perpendicular to an axial direction of the core wires, in the section, horizontal direction is defined as the direction of a tangent to the curved part of the first side portion and the curved part of the second side portion, height direction is defined as the direction perpendicular to the horizontal direction, with a crimp height that is the height from a bottom surface of the bottom portion to the tangent is $1.20\pm0.05$ mm and a crimp width that is the width in the horizontal direction of the holding portion is $1.66\pm0.05$ mm.

12. The method for manufacturing the crimp body according to claim 11, wherein
the preparing the crimp terminal and a lead wire includes preparing the crimp terminal such that a thicknesses of the first distal end portion and a thickness of the second distal end portion are smaller than a diameter of the core wires of the lead wire.

* * * * *